(12) United States Patent
Welman et al.

(10) Patent No.: US 10,729,707 B2
(45) Date of Patent: Aug. 4, 2020

(54) DAIRY PRODUCT AND PROCESS

(71) Applicant: FONTERRA CO-OPERATIVE GROUP LIMITED, Auckland (NZ)

(72) Inventors: Alan David Welman, Palmerston North (NZ); Geoffrey Stevens, Palmerston North (NZ); Christopher Paul McJarrow, Palmerston North (NZ); Bertram Yin Fong, Palmerston North (NZ); Bing Wang, New South Wales (AU)

(73) Assignee: Fonterra Co-Operative Group Limited, Auckland (NZ)

( * ) Notice: Subject to any disclaimer, the term of this patent is extended or adjusted under 35 U.S.C. 154(b) by 0 days.

(21) Appl. No.: 16/319,213

(22) PCT Filed: Jul. 28, 2017

(86) PCT No.: PCT/IB2017/054610
§ 371 (c)(1),
(2) Date: Jan. 18, 2019

(87) PCT Pub. No.: WO2018/020473
PCT Pub. Date: Feb. 1, 2018

(65) Prior Publication Data
US 2019/0247409 A1 Aug. 15, 2019

(30) Foreign Application Priority Data

Jul. 28, 2016 (NZ) ........................................ 722642

(51) Int. Cl.
| | |
|---|---|
| *A61K 31/702* | (2006.01) |
| *A23L 33/00* | (2016.01) |
| *A23C 9/142* | (2006.01) |
| *A23C 9/12* | (2006.01) |
| *A61P 25/00* | (2006.01) |
| *A23L 33/135* | (2016.01) |
| *A61P 25/28* | (2006.01) |
| *A61K 35/745* | (2015.01) |
| *A61K 35/747* | (2015.01) |
| *C12N 9/04* | (2006.01) |
| *C12N 9/38* | (2006.01) |

(52) U.S. Cl.
CPC .............. *A61K 31/702* (2013.01); *A23C 9/12* (2013.01); *A23C 9/1206* (2013.01); *A23C 9/142* (2013.01); *A23C 9/1422* (2013.01); *A23C 9/1427* (2013.01); *A23L 33/135* (2016.08); *A23L 33/40* (2016.08); *A61K 35/745* (2013.01); *A61K 35/747* (2013.01); *A61P 25/00* (2018.01); *A61P 25/28* (2018.01); *C12N 9/0006* (2013.01); *C12N 9/2471* (2013.01); *A23C 2210/20* (2013.01); *A23C 2210/206* (2013.01); *A23V 2002/00* (2013.01)

(58) Field of Classification Search
CPC ...... A61K 31/702; A23L 33/135; A23L 33/40
See application file for complete search history.

(56) References Cited

U.S. PATENT DOCUMENTS

| | | | | |
|---|---|---|---|---|
| 6,623,954 | B1 * | 9/2003 | Spade | ................. A23C 21/023 426/34 |
| 9,382,564 | B2 | 7/2016 | Dekany et al. | |
| 2007/0104843 | A1 | 5/2007 | Holst et al. | |
| 2011/0020304 | A1 | 1/2011 | Sprenger | |
| 2011/0129452 | A1 | 6/2011 | Rochat et al. | |
| 2012/0083600 | A1 | 4/2012 | Felo et al. | |
| 2012/0171165 | A1 | 7/2012 | Buck et al. | |
| 2012/0202753 | A1 | 8/2012 | Morrow et al. | |
| 2012/0208782 | A1 | 8/2012 | Frantz | |
| 2012/0231145 | A1 | 9/2012 | Sogame et al. | |

(Continued)

FOREIGN PATENT DOCUMENTS

| | | |
|---|---|---|
| AU | 2012/203568 | 7/2012 |
| AU | 2012/260945 | 10/2013 |

(Continued)

OTHER PUBLICATIONS

Martin-Sosa (Journal of Dairy Science; 2003; 86, 52-59).*
McGrath; Dairy Science and Technology (2016), 96; 133-158; published online Sep. 2015.*
Extended European Search Report in corresponding European Patent Application No. 17833689.7 dated Feb. 14, 2020 in 11 pages.
GEA Process Engineering, Membrane Filtration in the Dairy Industry, Published 2012, pp. 1-11.
Dairy Technology, Separation of Milk http://dairy-technology.blogspot.com/2014/01/separation-of-milk.html [Jul. 17, 2019 10:12:07 AM].

(Continued)

*Primary Examiner* — Pancham Bakshi
(74) *Attorney, Agent, or Firm* — Knobbe, Martens, Olson & Bear, LLP

(57) ABSTRACT

A method of producing sialyloligosaccharides a sialyloligosaccharides-containing source that also contains carbohydrates and minerals. The process includes subjecting the source to a temperature of from about 67° C. and (i) filtration with a heat-resistant filter at a temperature of about 35 to about 95° C. to produce a first retentate and first permeate, or (ii) centrifugal separation to produce a light phase and a heavy phase and filtration of the light phase at a temperature of about 50 to about 70° C. to produce a first retentate and first permeate, (b) nanofiltration of the first permeate, or nanofiltration and diafiltration of the first permeate, to produce a second retentate and second permeate, and (c) concentration of the second retentate, to produce a sialyloligosaccharide-containing extract. Additionally, the invention relates to a sialyloligosaccharide-enriched composition comprising at least 3'-sialyllactose and 6'-sialyllactose and its use in, for example, nutritional and infant formulas, and for maintaining or improving cognitive function.

10 Claims, 3 Drawing Sheets

(56) References Cited

U.S. PATENT DOCUMENTS

| | | |
|---|---|---|
| 2012/0245119 A1 | 9/2012 | Itoh et al. |
| 2012/0276208 A1 | 11/2012 | Best |
| 2013/0137643 A1 | 5/2013 | Zimmer et al. |
| 2013/0251844 A1 | 9/2013 | Sprenger et al. |
| 2014/0087021 A1 | 3/2014 | Berrocal et al. |
| 2014/0170293 A1 | 6/2014 | Holst et al. |
| 2015/0159231 A1 | 6/2015 | Doring |
| 2015/0231159 A1 | 8/2015 | Hernandez et al. |
| 2015/0265661 A1 | 9/2015 | Newburg |
| 2015/0320778 A1 | 11/2015 | Chow et al. |

FOREIGN PATENT DOCUMENTS

| | | |
|---|---|---|
| EP | 2465508 | 6/2012 |
| EP | 2465509 | 6/2012 |
| EP | 2880993 | 6/2015 |
| GB | 2468670 | 9/2010 |
| WO | WO 1998/015581 | 4/1998 |
| WO | WO 2001/060171 | 8/2001 |
| WO | WO 2009/113861 | 9/2009 |
| WO | WO 2010/106319 | 9/2010 |
| WO | WO 2011/040360 | 4/2011 |
| WO | WO 2011/096809 | 8/2011 |
| WO | WO 2013/057049 | 4/2013 |
| WO | WO 2014/100022 | 6/2014 |
| WO | WO 2014/100126 | 6/2014 |
| WO | WO 2014/100191 | 6/2014 |
| WO | WO 2014/100225 | 6/2014 |
| WO | WO 2014/141164 | 9/2014 |
| WO | WO 2015/041515 | 3/2015 |
| WO | WO 2015/164021 | 10/2015 |
| WO | WO 2016/029113 | 2/2016 |
| WO | WO 2016/146789 | 9/2016 |
| WO | WO 2017/220697 | 12/2017 |

OTHER PUBLICATIONS

International Search Report and Written Opinion dated Nov. 3, 2017 in corresponding PCT Application PCT/IB2017/054610 in 22 pages.

* cited by examiner

DAIRY PRODUCT AND PROCESS

FIELD OF THE INVENTION

The present invention relates to a method of obtaining sialyloligosaccharides, sialyloligosaccharide-enriched compositions and the use of sialyloligosaccharides for maintaining or increasing brain function or development.

BACKGROUND TO THE INVENTION

The composition of mammalian milk is specifically targeted to support normal growth and development of the infant or child (International Code of Marketing Breastmilk Substitutes, World Health Organisation, Geneva, 1981).

Maternal formulas, infant formulas, follow-on formulas, growing-up formulas, dietetic products and other dairy containing compositions are typically produced using non-human milk. However, the nutritional composition of human milk differs in some respects to that of non-human milk. Non-human whole milk such as cow, goat or sheep milk, contains a very different complement of milk oligosaccharides to that of human milk.

Optimal cognitive development and growth is a key part of infant and child development. Clearly, impaired cognitive development will have significant effects on quality of life. Additionally, restricted growth has been shown to have detrimental effects on long-term health. Therefore, any agent shown to increase cognitive development or maintain healthy growth will have wide benefits for infants and children (Bryan et al., (2004). Nutrients for cognitive development in school-aged children. *Nutr Rev* 62: 295-306).

Cognitive decline is characterised by reduced learning ability, memory and attention span is widespread among the elderly. Any agent that prevents or delays cognitive decline will have widespread benefits on the quality of life of the elderly.

It is an object of the present invention to provide a method of obtaining sialyloligosaccharides, sialyloligosaccharide-enriched compositions and the use of sialyloligosaccharides for maintaining or increasing brain function or development, or to at least provide the public with a useful choice.

SUMMARY OF THE INVENTION

In a first aspect, the invention provides a method of producing sialyloligosaccharides from a liquid source that comprises sialyloligosaccharides, carbohydrates and minerals by subjecting the liquid source to a process comprising
  a) heating the liquid source to a temperature of from about 67° C.,
  b) subjecting the heat-treated liquid source to
    (i) a filtration step with a heat-resistant filter at a temperature of about 35 to about 95° C. to produce a first retentate and first permeate, or
    (ii) centrifugal separation to produce a light phase and a heavy phase and filtration of the light phase with a heat-resistant filter at a temperature of about 35 to about 95° C. to produce a first retentate and first permeate,
  c) subjecting the first permeate to nanofiltration, or nanofiltration and diafiltration, to produce a second retentate and second permeate, and
  d) concentrating the second retentate, to produce a sialyloligosaccharide-containing extract.

In a further aspect the invention relates to a sialyloligosaccharide-enriched composition, comprising on a dry solids basis
  at least about 5% by weight total sialyloligosaccharides comprising
    at least about 5% 3'-sialyllactose by weight of total sialyloligosaccharides,
    at least about 2% 6'-sialyllactose by weight of total sialyloligosaccharides,
    at least about 0.01% disialyllactose by weight of total sialyloligosaccharides,
    at least about 0.01% sialyllactosamine by weight of total sialyloligosaccharides, and
  at least about 0.5% by weight free sialic acid,
  at least about 0.2% by weight neutral oligosaccharides,
  less than about 25% by weight protein and non-protein nitrogen,
  less than about 80% by weight sugars not including sialyllactose, and
  less than about 5% by weight ash.

In a further aspect the invention relates to a composition for providing nutrition to an infant of less than 6 months of age comprising 3'-sialyllactose, 6'-sialyllactose and sialyllactosamine in a ratio of from about 10:1:0.5 to about 1.5:1:0.03 3'-sialyllactose to 6'-sialyllactose.

In a further aspect the invention relates to a composition for providing nutrition to an infant of from about 6 months to about 12 months of age comprising 3'-sialyllactose, 6'-sialyllactose and sialyllactosamine in a ratio of from about 10:1:0.5 to about 1.5:1:0.03 3'-sialyllactose to 6'-sialyllactose.

In a further aspect the invention relates to a composition for providing nutrition to an infant of 12 months of age or over comprising 3'-sialyllactose, 6'-sialyllactose and sialyllactosamine in a ratio of from about 10:1:0.5 to about 1.5:1:0.03 3'-sialyllactose to 6'-sialyllactose.

In a further aspect the invention relates to method of treating mild cognitive impairment associated with any one or more of age-related cognitive decline, or cognitive impairment associated with any one or more of Alzheimer's disease, vascular disease, frontotemporal lobar degeneration (FTLD), Parkinson's disease, amyotrophic lateral sclerosis, Huntington's disease, cognitive impairment associated with schizophrenia, chemotherapy-induced neuropathy, Down's syndrome, Korsakoff's disease, cerebral palsy, epilepsy, neuronal ischemia, neuronal reperfusion injury, neuronal trauma, neuronal haemorrhage, neuronal infection, stroke, neuronal exposure to a toxic substance, age-related mental disorders, anxiety disorders, age-related depression, dementia associated with microvascular disorders (such as diabetes, hypotension, stroke induced vascular dementia, and obesity), dementia associated with a disorder of the immune system, dementia associated with a central nervous system (CNS) disorder, dementia associated with hypotension, dementia associated with obesity or vascular dementia comprising administering an effective amount of a sialyloligosaccharide-containing extract.

As used herein, "treating" includes preventing, delaying or ameliorating.

Any one or more of the following embodiments may relate to any of the aspects described herein or any combination thereof.

Preferably the liquid source comprises a combination of two or more sialyloligosaccharide-containing streams.

Preferably the liquid source comprises mother liquor as a by-product of lactose crystallisation, a dairy permeate, whey, whey permeate, or a combination of any two or more thereof.

Preferably the heat treatment is carried out at a temperature of from about 67 to about 100° C.

Preferably the heat treatment of the liquid source is carried out for about 2, 3, 4, 5, 6, 7, 8, 9, 10, 11, 12, 13, 14, 15, 16, 17, 18, 19 or 20 minutes, and suitable ranges may be selected from between any of these values.

Preferably the heat treatment of the liquid source precipitates about 2, 3, 4, 5, 6, 7, 8, 9 or 10% of the minerals present in the liquid source, and suitable ranges may be selected from between any of these values.

Preferably the first permeate comprises
less than about 96% of the minerals in the liquid source, and/or
less than about 20% of the protein in the liquid source.

Preferably the first retentate comprises
at least about 3% of the minerals in the liquid source, and/or
at least about 80% of the protein in the liquid source.

Preferably the filtration step results in a reduction in the amount of insoluble minerals and protein in the first permeate, when compared to the liquid source.

Preferably the filtration step of (b)(i) is carried out at about 50, 55, 60, 65, 70, 75, 80, 85 or 90° C. to produce a first retentate and first permeate, and suitable ranges may be selected from between any of these values.

Preferably the heat resistant filter of (b)(i) is a ceramic filter.

Preferably the filtration step of (b)(ii) is carried out at about 55, 60, 65, or about 70° C. to produce a first retentate and first permeate, and suitable ranges may be selected from between any of these values.

Preferably the filtration step of (b)(ii) is carried out using a heat resistant filter.

Preferably the heat resistant filter of (b)(ii) is a ceramic filter.

Preferably the heat treated liquid source is subjected to ultrafiltration with a ceramic filter.

Preferably the ceramic ultrafiltration is conducted at a temperature of from about 50, 55, 60, 65, 70, 75, 80, 85 or 90° C., and suitable ranges may be selected from between any of these values. Preferably the ceramic ultrafiltration is conducted at a temperature of from about 60° C. to about 80° C.

Preferably at least one glycoside hydrolase or polymerase enzyme reaction.

Preferably
a) the first permeate,
b) the light phase,
c) the concentrated second retentate, or
d) a combination of any two or more of (a) to (c),
is subjected to the enzyme reaction.

Preferably the enzyme reaction
a) increases the molecular size of at least one disaccharide in the source to produce at least one oligosaccharide, or
b) decreases the molecular size of at least one disaccharide in the source to produce one or more monosaccharides.

Preferably the enzyme comprises β-galactosidase.
Preferably the disaccharide comprises lactose.
Preferably the monosaccharide comprises galactose or glucose.
Preferably the oligosaccharide comprises one or more galactooligosaccharides.

Preferably the filtration of the light phase is ultrafiltration.

Preferably the ultrafiltration is conducted at a temperature of from about 50, 55, 60, 65 or 70° C., and suitable ranges may be selected from between any of these values. Preferably the ultrafiltration is conducted at a temperature of from about 55° C. to about 65° C.

Preferably the nanofiltration is conducted at a temperature of from about 25, 30, 35, 40, 45, 50 or 55° C., and suitable ranges may be selected from between any of these values. Preferably the ultrafiltration is conducted at a temperature of about 50° C.

Preferably the second permeate comprises soluble minerals and at least one monosaccharide or disaccharide.

Preferably the second retentate comprises
less than about 70% of the minerals in the first permeate, or
less than about 50% of the non-sialyloligosaccharide sugars in the first permeate.

Preferably the second retentate comprises
at least about 7% by weight sialyloligosaccharides,
at least about 0.2% by weight neutral oligosaccharides,
less than about 5% by weight protein and non-protein nitrogen,
less than about 80% by weight non-sialyloligosaccharide sugars, and
less than about 5% by weight ash.

Preferably the second permeate comprises
at least about 30% of the minerals in the first permeate, or
at least about 50% of the non-sialyloligosaccharide sugars in the first permeate.

Preferably the second retentate is subjected to either nanofiltration or reverse osmosis to produce a third retentate.

Preferably the concentrated second retentate, or the third retentate, is subjected to decolourisation.

Preferably the method comprises the steps of
subjecting the sialyloligosaccharide-containing extract to crystallisation to produce a crystallised sialyloligosaccharide-containing extract, and
drying the sialyloligosaccharide-containing extract or crystallised sialyloligosaccharide-containing extract to produce a dried sialyloligosaccharide-containing extract.

Preferably the sialyloligosaccharide-containing extract comprises less than about 20, 19, 18, 17, 16, 15, 14, 13, 12, 11, 10, 9, 8, 7, 6, 5, 4 3, 2, or 1% by weight protein and non-protein nitrogen, and suitable ranges may be selected from between any of these values.

Preferably the sialyloligosaccharide-containing extract comprises less than about 15, 14, 13, 12, 11, 10, 9, 8, 7, 6, 5, 4, 3, 2, 1% by weight ash, and suitable ranges may be selected from between any of these values.

Preferably the sialyloligosaccharide-containing extract comprises, on a dry solids basis
at least about 7% by weight sialyloligosaccharides,
at least about 0.2% by weight neutral oligosaccharides,
less than about 5% by weight protein and non-protein nitrogen,
less than about 80% by weight non-sialyloligosaccharide sugars, and
less than about 5% by weight ash.

Preferably the sialyloligosaccharide-containing extract comprises, on a dry solids basis
at least about 5% by weight 3'-sialyllactose, and
at least about 2% by weight 6'-sialyllactose.

In a further aspect the invention relates to a sialyloligosaccharide-containing extract produced by any one of the methods described above.

Preferably the composition comprises, on a dry solids basis, a greater amount of 3'-sialyllactose relative to the amount of 6'-sialyllactose.

Preferably the composition comprises 3'-sialyllactose and 6'-sialyllactose in a ratio of from about 65:1 to about 1.5:1, from about 15:1 to about 1.5:1, or from about 8:1 to about 1.5:1, and suitable ranges may be selected from between any of these values.

In a further aspect the invention relates to a nutritional formulation comprising a sialyloligosaccharide-containing extract produced by a method as described above, or comprises a sialyloligosaccharide-enriched composition as described above.

Preferably the nutritional formulation is an infant formula, a follow-on formula, a growing-up formula, a paediatric formula, a human milk fortifier, a children's food or drink, a maternal supplement, a maternal nutritional formulation, a fermented food, a UHT milk, a UHT drinking yoghurt, an acidified milk drink, a UHT powder, a medical food, a sports nutritional formulation, or a formulation for senior or aged populations.

Preferably the nutritional formulation comprises one or more dairy lipids, one or more galactooligosaccharides, one or more probiotic strains, one or more protein hydrolysates, lactoferrin, a milk fat globular membrane (MFGM) formulation, other prebiotics, or a combination of any two or more thereof.

Preferably the nutritional formulation the dairy lipid comprises buttermilk, high fat whey protein concentrate, beta-serum, butter serum, or a combination of any two or more thereof.

Preferably the probiotic strain comprises a *Bifidobacterium lactis* or a *Lactobacillus rhamnosus* strain, or a combination of both *Bifidobacterium lactis* and *Lactobacillus rhamnosus*.

Preferably the *Bifidobacterium lactis* strain comprises *Bifidobacterium lactis* HN019 (DR10™).

Preferably the *Lactobacillus rhamnosus* strain comprises *Lactobacillus rhamnosus* HN001 (DR20™).

In a further aspect the invention relates to a method of maintaining or increasing brain function or brain development, the method comprising administering (i) an effective amount of a sialyloligosaccharide-containing extract produced by the method as described above, or (ii) a nutritional formulation as described above, to a normal subject.

Preferably the sialyloligosaccharide-containing extract comprises
a) one or more structural glycoconjugates of sialic acid,
b) free sialic acid, or
c) both (a) and (b).

Preferably the extract, composition or nutritional formulation is administered to
a) prevent delayed brain development,
b) maintain the viability or function of neuronal cells,
c) maintain or increase cognitive development,
d) prevent delayed cognitive development,
e) maintain or increase cognitive performance,
f) prevent cognitive decline,
g) maintain or increase learning, memory or attention span,
h) prevent decline of learning ability, memory or attention span,
i) maintain or increase ability to cope with stress,
j) maintain or increase the level of neural cell adhesion molecule (NCAM),
k) prevent decline in brain function,
l) maintain or increase the level of gangliosides in the brain,
m) maintain or increase blood, nutrient or oxygen flow to the brain,
n) maintain or increase synaptogenesis,
o) maintain or increase the activity of the gut/brain axis,
p) maintain or increase neurogenesis in an older brain,
q) maintain or increase white matter volume, or
r) a combination of any two or more of a) to q).

Preferably the subject is a foetal, infant or child subject.

Preferably the extract, composition or nutritional formulation is administered to a mother during gestation to maintain or increase brain function or development in a foetal subject.

Preferably the extract, composition or formulation is administered to a breastfeeding mother to maintain or increase brain function or development in an infant subject.

In one embodiment the administration of the composition of the invention to an individual leads to an increase in glycerophosphorylcholine (GPC) in the brain in that individual of at least about 10, 15, 20, 25, 30, 35, 40 or 50%, and suitable ranges may be selected from between any of these values.

In one embodiment the administration of the composition of the invention to an individual leads to an increase in glutamine (Glu) in the brain in that individual of at least about 10, 15, 20, 25, 30, 35, 40 or 50%, and suitable ranges may be selected from between any of these values.

In one embodiment the administration of the composition of the invention to an individual leads to an increase in myo inositol (Ins) in the brain in that individual of at least about 10, 15, 20, 25, 30, 35, 40 or 50%, and suitable ranges may be selected from between any of these values.

In one embodiment the administration of the composition of the invention to an individual leads to a decrease in Lip09 in the brain in that individual of at least about 10, 15, 20, 25, 30, 35, 40 or 50%, and suitable ranges may be selected from between any of these values.

In one embodiment the administration of the composition of the invention to an individual leads to a decrease in macromolecules (MM) in the brain in that individual of at least about 10, 15, 20, 25, 30, 35, 40 or 50%, and suitable ranges may be selected from between any of these values.

In one embodiment the administration of the composition of the invention to an individual leads to an increase in N-Acetylaspartylglutamic acid (NAAG) in the brain in that individual of at least about 10, 15, 20, 25, 30, 35, 40 or 50%, and suitable ranges may be selected from between any of these values.

In one embodiment the administration of the composition of the invention to an individual leads to an increase in the glutamate-glutamine complex (Glx) in the brain in that individual of at least about 10, 15, 20, 25, 30, 35, 40 or 50%, and suitable ranges may be selected from between any of these values.

In a further aspect the invention relates to a method of treating mild cognitive impairment associated with any one or more of age-related cognitive decline, dementia, Alzheimer's disease, vascular disease, frontotemporal lobar degeneration (FTLD), dementia with Lewy bodies, Parkinson's disease, amyotrophic lateral sclerosis, Huntington's disease, cognitive impairment associated with schizophrenia, chemotherapy-induced neuropathy, Down's syndrome, Korsakoff's disease, cerebral palsy, epilepsy, neuronal ischemia, neuronal reperfusion injury, neuronal trauma, neuronal haemorrhage, neuronal infection, stroke, neuronal exposure to a toxic substance, age-related mental disorders, anxiety disorders, age-related depression, dementia associated with microvascular disorders (such as diabetes, hypotension, stroke induced vascular dementia, and obesity), dementia associated with a disorder of the immune system, dementia associated with a central nervous system (CNS) disorder, dementia associated with hypotension, dementia associated with obesity or vascular dementia comprising administering an effective amount of a sialyloligosaccharide-containing extract produced by the method of any one of claims 1 to 32, an extract or composition of any one of claims 33 to 36 or 44 to 46, or a nutritional formulation of any one of claims 37 to 43 to a subject in need thereof.

In a further aspect the invention relates to a sialyloligosaccharide-containing extract produced by a method of any one of claims 1 to 32, a composition of any one of claims 33 to 38 or 44 to 46, or a nutritional formulation of any one of claims 37 to 43 for treating mild cognitive impairment associated with any one or more of age-related cognitive decline, dementia, Alzheimer's disease, vascular disease, frontotemporal lobar degeneration (FTLD), dementia with Lewy bodies, Parkinson's disease, amyotrophic lateral sclerosis, Huntington's disease, cognitive impairment associated with schizophrenia, chemotherapy-induced neuropathy, Down's syndrome, Korsakoff's disease, cerebral palsy, epilepsy, neuronal ischemia, neuronal reperfusion injury, neuronal trauma, neuronal haemorrhage, neuronal infection, stroke, neuronal exposure to a toxic substance, age-related mental disorders, anxiety disorders, age-related depression, dementia associated with microvascular disorders (such as diabetes, hypotension, stroke induced vascular dementia, and obesity), dementia associated with a disorder of the immune system, dementia associated with a central nervous system (CNS) disorder, dementia associated with hypotension, dementia associated with obesity or vascular dementia.

In a further aspect the invention relates to a the use of a sialyloligosaccharide-containing extract produced by the method of any one of claims 1 to 32, or a composition of any one of claims 33 to 36 or 44 to 46, in the manufacture of a formulation for treating mild cognitive impairment associated with any one or more of age-related cognitive decline, dementia, Alzheimer's disease, vascular disease, frontotemporal lobar degeneration (FTLD), dementia with Lewy bodies, Parkinson's disease, amyotrophic lateral sclerosis, Huntington's disease, cognitive impairment associated with schizophrenia, chemotherapy-induced neuropathy, Down's syndrome, Korsakoff's disease, cerebral palsy, epilepsy, neuronal ischemia, neuronal reperfusion injury, neuronal trauma, neuronal haemorrhage, neuronal infection, stroke, neuronal exposure to a toxic substance, age-related mental disorders, anxiety disorders, age-related depression, dementia associated with microvascular disorders (such as diabetes, hypotension, stroke induced vascular dementia, and obesity), dementia associated with a disorder of the immune system, dementia associated with a central nervous system (CNS) disorder, dementia associated with hypotension, dementia associated with obesity or vascular dementia.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7).

This invention may also be said broadly to consist in the parts, elements and features referred to or indicated in the specification of the application, individually or collectively, and any or all combinations of any two or more of said parts, elements or features, and where specific integers are mentioned herein which have known equivalents in the art to which this invention relates, such known equivalents are deemed to be incorporated herein as if individually set forth.

In this specification, where reference has been made to external sources of information, including patent specifications and other documents, this is generally for the purpose of providing a context for discussing the features of the present invention. Unless stated otherwise, reference to such sources of information is not to be construed, in any jurisdiction, as an admission that such sources of information are prior art or form part of the common general knowledge in the art.

The term "comprising" as used in this specification means "consisting at least in part of". When interpreting statements in this specification which include that term, the features, prefaced by that term in each statement, all need to be present but other features can also be present. Related terms such as "comprise" and "comprised" are to be interpreted in the same manner.

BRIEF DESCRIPTION OF THE DRAWINGS

The invention will now be described by way of example only and with reference to the drawings in which.

DETAILED DESCRIPTION OF THE INVENTION

Figure 1:
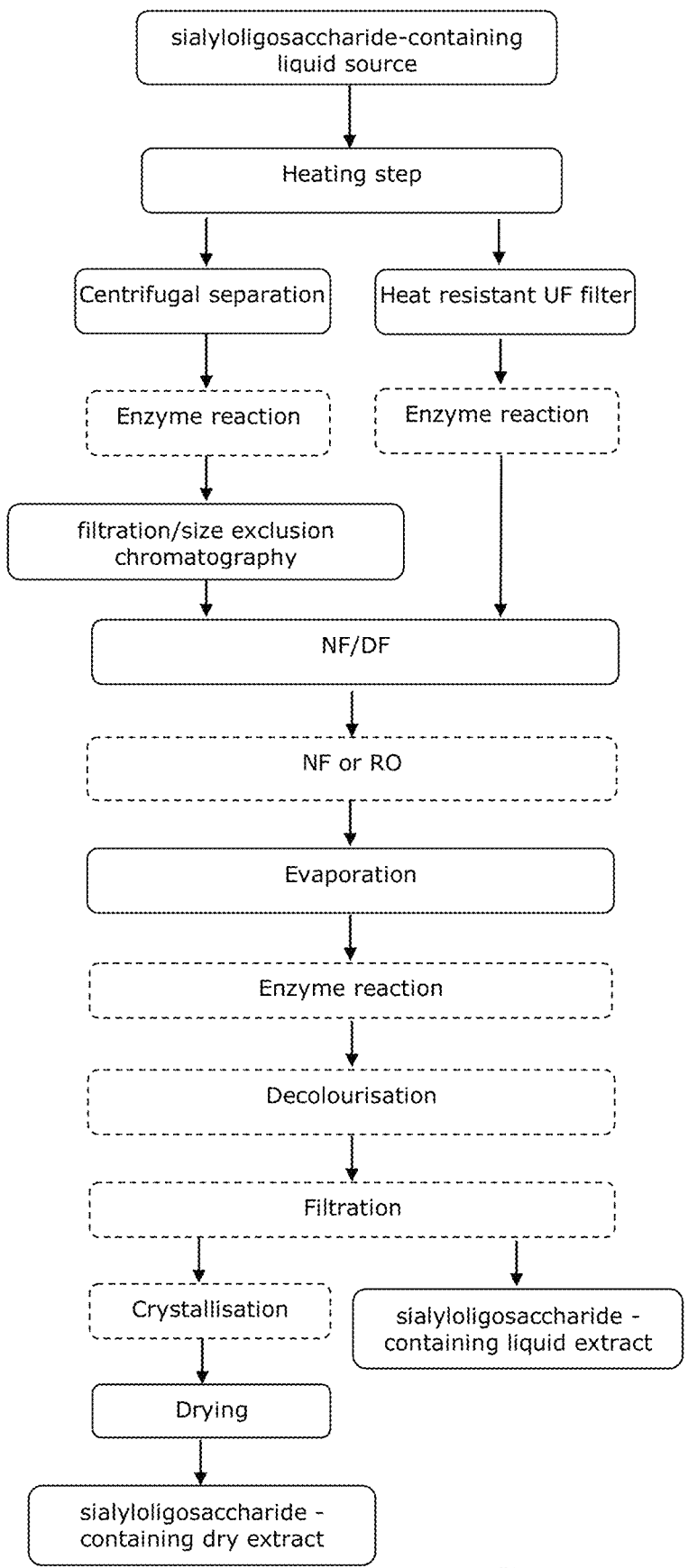
FIG. 1 shows a process flow diagram of the method for producing a sialyloligosaccharide-containing extract.
Figure 2:
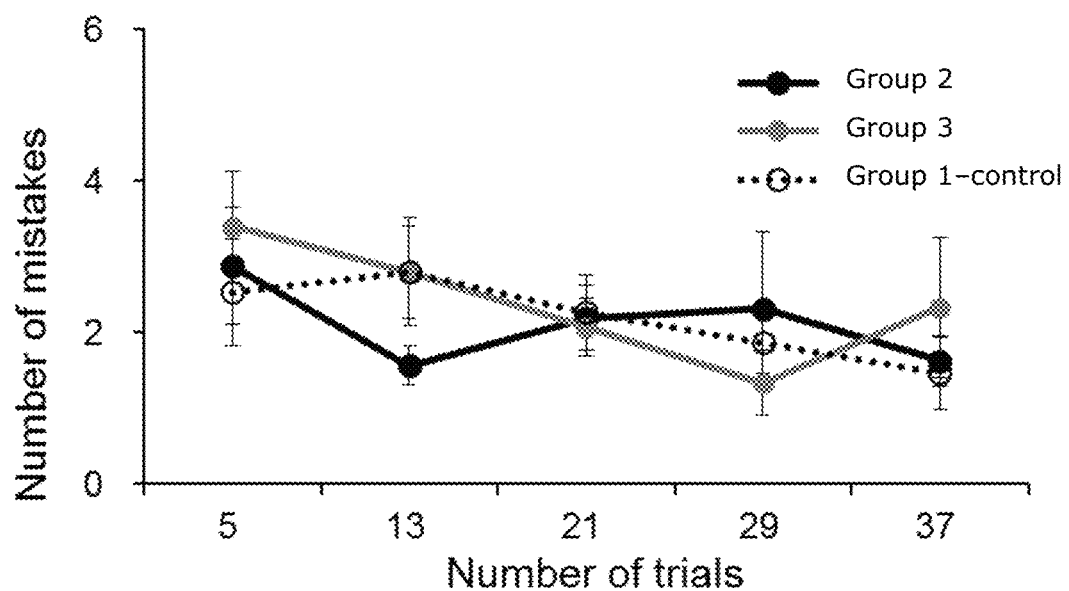
FIG. 2 shows a graph reporting the results of discrimination tests using a 3 hour "easy" task using an 8-arm radial maze.

The present invention relates to a method for the production of sialyloligosaccharide-enriched extracts for use in nutritional formulations including infant formulas.

The present invention also provides sialyloligosaccharide-enriched compositions, nutritional formulations comprising such compositions and uses of the compositions and nutritional formulations.

The various embodiments of the composition and methods of the invention have numerous advantages, including but not limited to the production of a high concentration sialyloligosaccharide composition that is low in impurities.

1. Source Material

The sialyloligosaccharide-containing liquid source for use in the invention is obtained from mammalian milk. It should be appreciated that any fraction or milk derivative can be utilised in the invention provided it contains sialyloligosaccharides.

In some embodiments, the sialyloligosaccharide-containing liquid source is derived from any mammalian milk including but not limited to bovine, sheep, goat, pig, mouse, water buffalo, camel, yak, horse, donkey, llama or human milk fat, with bovine milk being a preferred source.

In some embodiments the mammalian milk source is processed to remove at least protein and fat prior to being used in the inventive process.

By way of example, the sialyloligosaccharide-containing source may be generated from upstream milk processes, such as cheese manufacture or casein manufacture that produce a permeate. Examples of upstream milk processes include the production of cheese whey, rennet (sweet) whey, or ultrafiltration of skim or raw milk. After ultrafiltration of whey protein the protein is retained in the whey retentate and the whey permeate contains sialyloligosaccharides, lactose and minerals, since sialyloligosaccharides, lactose and minerals pass though the ultrafiltration membrane.

The sialyloligosaccharide-containing liquid source (e.g. permeate from upstream dairy processing) may then be processed by one or more filtration steps and may include one or more concentration steps.

In some embodiments the sialyloligosaccharide-containing liquid source comprises the permeate resulting from filtration of whole milk, recombined, powdered or fresh skim milk, recombined or reconstituted whole or skim milk powder, skim milk concentrate, skim milk retentate, concentrated milk, ultrafiltered milk retentate, colostrum, whey (including sweet whey, lactic acid whey, mineral acid whey, reconstituted whey powder or deproteinated whey), a composition derived from any milk processing stream, a composition derived from the permeate obtained by ultrafiltration or microfiltration of any milk processing stream, or a combination of any two or more thereof.

In one embodiment, the sialyloligosaccharide-containing liquid source comprises the permeate from upstream dairy processing processed by one or more filtration steps and/or concentration steps. In one embodiment, the sialyloligosaccharide-containing liquid source comprises the mother liquor produced as a by-product of lactose crystallisation. Following lactose crystallisation, the crystallised lactose is separated from the remaining solution. The remaining solution, the mother liquor (also known as delactosed permeate or Delac), comprises lactose, sialyloligosaccharides and minerals.

In one embodiment the sialyloligosaccharide-containing liquid source comprises one or more sialyloligosaccharide-containing streams.

In various embodiments the sialyloligosaccharide-containing liquid source comprises the mother liquor of lactose crystallisation (delactosed permeate), a dairy permeate, whey, whey permeate, or a combination of any two or more thereof.

In various embodiments the sialyloligosaccharide-containing liquid source comprises at least about 0.2, 0.5, 1, 2, 4, 6, 8, 10 or 12% by weight sialyloligosaccharides, and suitable ranges may be selected from between any of these values, (for example, about 0.2 to about 12, about 0.2 to about 8, about 0.2 to about 6, about 0.2 to about 4, about 0.5 to about 12, about 0.5 to about 10, about 0.5 to about 6, about 0.5 to about 2, about 1 to about 12, about 1 to about 10, about 1 to about 4, about 2 to about 12, about 2 to about 8, about 2 to about 6, about 4 to about 12, about 4 to about 10, about 4 to about 6, about 6 to about 12, about 6 to about 10 or about 8 to about 12% by weight sialyloligosaccharides).

In various embodiments the sialyloligosaccharide-containing liquid source comprises less than about 0.01, 0.05, 0.1, 0.2, 0.25, 0.3, 0.4, 0.5, 0.75, 1, 1.25, 1.5, 1.75, 2 or 2.25% by weight protein and non-protein nitrogen, and suitable ranges may be selected from between any of these values, (for example, from about 0.01 to about 2.25, about 0.01 to about 1.5, about 0.01 to about 1.25, about 0.01 to about 0.5, about 0.01 to about 0.3, about 0.01 to about 0.2, about 0.05 to about 2.25, about 0.05 to about 2, about 0.05 to about 1.5, about 0.05 to about 0.75, about 0.05 to about 0.4, about 0.05 to about 0.25, about 0.1 to about 2.25, about 0.1 to about 1.75, about 0.1 to about 1.25, about 0.1 to about 0.75, about 0.1 to about 0.5, about 0.2 to about 2.25, about 0.2 to about 2, about 0.2 to about 0.75, about 0.2 to about 0.5, about 0.25 to about 2.25, about 0.25 to about 2, about 0.25 to about 1.5, about 0.25 to about 1.25, about 0.25 to about 1, about 0.25 to about 0.75, about 0.3 to about 2.25, about 0.3 to about 2, about 0.3 to about 1.5, about 0.3 to about 1, about 0.3 to about 0.75, about 0.4 to about 2.25, about 0.4 to about 2, about 0.4 to about 1, about 0.4 to about 0.75, about 0.5 to about 2.25, about 0.5 to about 2, about 0.5 to about 1.75, about 0.5 to about 1, about 0.75 to about 2.25, about 0.75 to about 2, about 0.75 to about 1.5, about 1 to about 2.25, about 1 to about 1.75, about 1 to about 1.5, about 1.25 to about 2.25, about 1.25 to about 1.75, about 1.25 to about 1.5, about 1.5 to about 2.25, about 1.5 to about 2 or about 1.75 to about 2.25% by weight protein)

In various embodiments the sialyloligosaccharide-containing liquid source comprises less than about 10, 20, 25, 30, 35, 40, 45, 50, 55, 60, 65, 70 or at least about 75% by weight non-sialyloligosaccharide sugars, and suitable ranges may be selected from between any of these values, (for example, from about 10 to about 75, about 10 to about 70, about 10 to about 65, about 10 to about 60, about 20 to about 75, about 20 to about 70, about 20 to about 65, about 20 to about 60, about 30 to about 75, about 30 to about 70, about 30 to about 65, about 30 to about 60, about 40 to about 75, about 40 to about 70, about 40 to about 65, or about 40 to about 60% by weight non-sialyloligosaccharide sugars).

In various embodiments the sialyloligosaccharide-containing liquid source comprises 3'-sialyllactose and 6'-sialyllactose in a ratio of about 65:1, 50:1, 40:1, 30:1, 25:1, 20:1, 15:1, 14:1, 13:1, 12:1, 11:1, 10:1, 9:1, 8:1, 7:1, 6:1, 5:1, 4:1, 3:1, 2:1, 1.5:1 or 1.5:1 and suitable ranges may be selected from between any of these values, (for example, from about 65:1 to about 1.5:1, about 65:1 to about 1.5:1, about 65:1 to about 3:1, about 65:1 to about 7:1, about 65:1 to about 9:1, about 65:1 to about 13:1, about 65:1 to about 15:1, about 65:1 to about 20:1, about 50:1 to about 1.5:1, about 50:1 to about 1.5:1, about 50:1 to about 3:1, about 50:1 to about 7:1, about 50:1 to about 9:1, about 50:1 to about 13:1, about 50:1 to about 15:1, about 50:1 to about 20:1, about 40:1 to about 1.5:1, about 40:1 to about 1.5:1, about 40:1 to about 3:1, 40:1 to about 7:1, about 40:1 to about 9:1, about 40:1 to about 13:1, about 40:1 to about 15:1, about 40:1 to about 20:1, about 30:1 to about 1.5:1, about 30:1 to about 1.5:1, about 30:1 to about 3:1, about 30:1 to about 7:1, about 30:1 to about 9:1, about 30:1 to about 13:1, about 30:1 to about 15:1, about 30:1 to about 20:1, about 25:1 to about 1.5:1, about 25:1 to about 1.5:1, about 25:1 to about 4:1, about 25:1 to about 8:1, about 25:1 to about 10:1, about 25:1 to about 12:1, about 25:1 to about 14:1, about 25:1 to about 20:1, about 20:1 to about 1.5:1, about 20:1 to about 1.5:1, about 20:1 to about 3:1, about 20:1 to about 8:1, about 20:1 to about 11:1, 20:1 to about 15:1, 15:1 to about 1.5:1, about 15:1 to about 1.5:1, about 15:1 to about 2:1, about 12:1 to about 1.5:1, about 12:1 to about 1.5:1, about 12:1 to about 2:1, about 10:1 to about 1.5:1, about 10:1 to about 1.5:1, about 10:1 to about 2:1, about 8:1 to about 1.5:1, about 8:1 to about 1.5:1, about 18:1 to about 2:1, about 7:1 to about 1.5:1, about 7:1 to about 1.5:1, about 7:1 to about 2:1, about 6:1 to about 1.5:1, about 6:1 to about 1.5:1, about 6:1 to about 2:1, about 5:1 to about 1.5:1, from about 15:1 to about 1:1, about 12:1 to about 1:1, about 10:1 to about 1:1, about 8:1 to about 1:1, about 7:1 to about 1:1, about 6:1 to about 1:1, about 5:1 to about 1:1, about 15:1 to about 2:1, about 12:1 to about 2:1, about 10:1 to about 2:1, about 8:1 to about 2:1, about 7:1 to about 2:1, about 6:1 to about 2:1, about 5:1 to about 2:1, about 15:1 to about 3:1, about 12:1 to about 3:1, about 10:1 to about 3:1, about 8:1 to about 3:1, about 7:1 to about 3:1, about 6:1 to about 3:1, or about 5:1 to about 3:1.

In those embodiments where the sialyloligosaccharide-containing liquid source is a mother liqueur then the ratio of 3'-sialyllactose and 6'-sialyllactose is about 15:1, 14:1, 13:1, 12:1, 11:1, 10:1, 9:1, 8:1, 7:1, 6:1, 5:1, 4:1, 3:1, 2:1, 1.5:1 or 1.5:1 and suitable ranges may be selected from between any of these values, (for example, from about 15:1 to about 1.5:1, about 12:1 to about 1.5:1, about 10:1 to about 1.5:1, about 8:1 to about 1.5:1, about 7:1 to about 1.5:1, about 6:1 to about 1.5:1, about 5:1 to about 1.5:1, from about 15:1 to about 1:1, about 12:1 to about 1:1, about 10:1 to about 1:1, about 8:1 to about 1:1, about 7:1 to about 1:1, about 6:1 to about 1:1, about 5:1 to about 1:1, about 15:1 to about 2:1, about 12:1 to about 2:1, about 10:1 to about 2:1, about 8:1 to about 2:1, about 7:1 to about 2:1, about 6:1 to about 2:1, about 5:1 to about 2:1, about 15:1 to about 3:1, about 12:1 to about 3:1, about 10:1 to about 3:1, about 8:1 to about 3:1, about 7:1 to about 3:1, about 6:1 to about 3:1, or about 5:1 to about 3:1).

2. Removal of Insoluble Minerals and Protein

The first step of the method removes at least insoluble minerals and protein from the sialyloligosaccharide-containing source. In some embodiments the first step also removes fat from the sialyloligosaccharide-containing source.

In one embodiment the sialyloligosaccharide-containing liquid source is heated to a temperature of at least about 60, 61, 62, 63, 64, 65, 66, 67, 68, 69, 70, 71, 72, 73, 74, or at least about 75° C. to precipitate minerals in the source. The temperature may be controlled during this step by injection of steam or water, or both steam and water.

In some embodiments the sialyloligosaccharide-containing liquid source is heated for a period of at least about 30, 60 or 90 seconds, or at least about 2, 3, 4, 5, 6, 7, 8, 9 or 10 minutes. Preferably the heating step is carried out for about 5 min.

In some embodiments the heat treatment of the liquid source precipitates about 2, 3, 4, 5, 6, 7, 8, 9 or 10% of the minerals present in the liquid source, and suitable ranges may be selected from between any of these values, (for example, about 2 to about 10, about 2 to about 8, about 2 to about 6, about 3 to about 10, about 3 to about 9, about 3 to about 8, about 3 to about 6, about 4 to about 10, about 4 to about 8, about 4 to about 6%).

In various embodiments the sialyloligosaccharide-containing liquid source is subjected to a demineralisation step to remove insoluble minerals from the source.

In one embodiment the insoluble minerals, including any precipitated minerals produced by heating, are removed by centrifugation. Other suitable methods for removing insoluble minerals may be used as will be readily apparent to those skilled in the art.

In some embodiments the demineralisation step also removes protein from the sialyloligosaccharide-containing liquid source.

In some embodiments the demineralised liquid source is concentrated using any of the methods described below.

In some embodiments, filtration is used to remove at least protein. In other embodiments filtration is used to remove at least insoluble minerals and protein.

Ceramic Filtration

In various embodiments ceramic filtration is used to remove insoluble minerals and protein from the sialyloligosaccharide-containing liquid source. Ceramic filtration separates the protein and insoluble minerals retained in the filtration retentate from the lactose, oligosaccharides and soluble minerals contained in the filtration permeate.

In one embodiment the sialyloligosaccharide-containing liquid source is heated to precipitate minerals in the source as described above before ceramic filtration is performed at a temperature of about 35 to about 95° C.

In one embodiment the sialyloligosaccharide-containing liquid source is heated to precipitate minerals in the source as described above, followed by centrifugation and then ceramic filtration light phase at a temperature of about 50 to about 70° C. is performed.

In one exemplary embodiment the method comprises ceramic ultrafiltration.

In various embodiments the method comprises ceramic filtration using a ceramic membrane comprising aluminium oxide or zirconium oxide.

In various embodiments the ceramic filtration is conducted using a membrane having a molecular weight cutoff of at least about 500, 600, 700, 750, 800, 900, 1,000, 1,100, 1,200, 1,250, 1,300, 1,400, 1,500, 1,750, 2,000, 2,500, 5,000, 10,000, 15,000, 20,000, 25,000, 30,000, 50,000, 100,000, 150,000 or 200,000 Da and useful ranges may be selected from between any of these values, (for example, from about 500 to about 200,000, about 500 to about 100,000, about 500 to about 30,000, about 500 to about 10,000, about 500 to about 5,000, about 500 to about 2,500, about 500 to about 2,000, about 500 to about 1,500, from about 750 to about 200,000, about 750 to about 100,000, 750 to about 30,000, about 750 to about 10,000, about 750 to about 5,000, about 750 to about 2,500, about 750 to about 2,000, about 750 to about 1,500, from about 1,000 to about 200,000, about 1,000 to about 100,000, about 1,000 to about 30,000, about 1,000 to about 10,000, about 1,000 to about 5,000, about 1,000 to about 2,500, about 1,000 to about 2,000, or about 1,000 to about 1,500 Da).

In various embodiments the ceramic filtration is conducted using a membrane having a pore size of at least about 0.001, 0.005, 0.01, 0.05, 0.1, 0.25, 0.4, 0.5, 0.6, 0.75, 0.8, 1, 1.25, 1.4, 1.5, 1.6, 1.75, 1.8, 2, 2.5 or 3 μm and useful ranges may be selected from between any of these values, (for example, from about 0.001 to about 3, about 0.001 to about 2.5, about 0.001 to about 2, 0.001 to about 1.75, 0.001 to about 1.5, about 0.005 to about 3, about 0.005 to about 2.5, about 0.005 to about 2, 0.005 to about 1.75, 0.005 to about 1.5, about 0.01 to about 3, about 0.01 to about 2.5, about 0.01 to about 2, 0.01 to about 1.75, or from about 0.01 to about 1.5 μm).

In various embodiments ceramic filtration is conducted at a temperature of at least about 30, 35, 40, 45, 50, 55, 60, 65, 70, 75, 80, 85, 90 or 95° C., and useful ranges may be selected from between any of these values, (for example, from about 30 to about 95, about 40 to about 95, about 50 to about 95, about 40 to about 90, about 50 to about 90, about 60 to about 90, about 65 to about 90, about 40 to about 85, about 50 to about 85, about 55 to about 85, about 60 to about 90, about 65 to about 90, about 40 to about 80, about 50 to about 80, about 55 to about 80, about 60 to about 80, about 65 to about 80, about 40 to about 75, about 50 to about 75, about 55 to about 75, about 60 to about 75, or about 65 to about 75° C.).

In various embodiments ceramic filtration is conducted at a pressure of at least about 1, 2, 3, 4, 5, 6, 7, 8, 9, 10, 11, 12, 13, 14, or 15 bar, and useful ranges may be selected from between any of these values, (for example, from about 1 to about 15, about 2 to about 15, about 3 to about 15, about 1 to about 12, about 3 to about 12, about 1 to about 10, about 3 to about 10, about 1 to about 8, about 2 to about 8, about 3 to about 8, about 1 to about 7, about 2 to about 7, about 3 to about 7, about 1 to about 6, about 2 to about 6, about 3 to about 6, about 1 to about 5, about 2 to about 5, or about 3 to about 5 bar).

In one embodiment the method comprises ceramic filtration in combination with diafiltration.

Other Filtration Methods

In various embodiments ultrafiltration or nanofiltration is used to remove at least protein. Filtration may be used to separate the protein, which is retained in the filtration retentate, from saccharides such as lactose and soluble minerals contained in the filtration permeate.

In some embodiments ultrafiltration or nanofiltration is used in combination with diafiltration.

Surprisingly, it has been found that ultrafiltration performed at high temperature leads to an improved yield in downstream processing steps, for example, an improved sialyloligosaccharide yield in the nanofiltration retentate and the final sialyloligosaccharide-containing extract. Increasing UF temperature from about 10° C. to about 50° C. increases sialyloligosaccharide yield by about 100% in the process. Increasing UF temperature from about 10° C. to about 65° C. increases sialyloligosaccharide yield by about 130%. Increasing UF temperature above about 65° C. will increase sialyloligosaccharide yield but in smaller increments than if increased up to 65° C.

In various embodiments ultrafiltration is conducted at a temperature of at least about 25, 30, 35, 40, 45, 50, 55, 60, 65, 70, 75, 80, 85 or 90° C., and useful ranges may be selected from between any of these values, (for example, from about 25 to about 90, about 40 to about 90, about 50 to about 90, about 30 to about 85, about 40 to about 85, about 50 to about 85, about 55 to about 85, about 30 to about 80, about 40 to about 80, about 50 to about 80, about 55 to about 80, about 30 to about 75, about 40 to about 75, about 50 to about 75, about 55 to about 75, about 30 to about 70, about 40 to about 70, about 50 to about 70, about 55 to about 70, about 30 to about 65, about 65 to about 75, about 50 to about 65, or about 55 to about 65° C.).

Suitable membranes for ultrafiltration include polyethersulfone membranes. Other ultrafiltration membranes known in the art may also be suitable as will be apparent to those skilled in the art.

In various embodiments ultrafiltration is conducted using a membrane having a molecular weight cutoff of at least about 1,000, 1,500, 2,000, 3,000, 3,500, 4,000, 5,000, 6,000, 7,000, 8,000, 9,000, 10,000, 12,500, 15,000, 17,500, 20,000, 25,000 or 30,000 Da, and useful ranges may be selected from between any of these values, for example, (from about 1,000 to about 30,000, about 3,000 to about 30,000, about 5,000 to about 30,000, about 1,000 to about 25,000, about 2,000 to about 25,000, about 3,000 to about 25,000, about 5,000 to about 25,000, about 1,000 to about 20,000, about 2,000 to about 20,000, about 3,000 to about 20,000, about 5,000 to about 20,000, about 10,000 to about 20,000, about 2,000 to about 15,000, about 3,000 to about 15,000, about 5,000 to about 15,000, about 2,000 to about 10,000, about 3,000 to about 10,000, or about 5,000 to about 10,000 Da).

In various embodiments ultrafiltration is conducted at a pressure of at least about 1, 2, 3, 4, 5, 6, 7, 8, 9, 10, 11, 12, 13, 14, or 15 bar, and useful ranges may be selected from between any of these values, (for example, from about 1 to about 15, about 2 to about 15, about 3 to about 15, about 4 to about 15, about 5 to about 15, about 1 to about 12, about 2 to about 10, about 3 to about 10, about 4 to about 10, about 5 to about 10, about 1 to about 8, about 2 to about 8, about 3 to about 8, about 4 to about 8, about 5 to about 8, about 1 to about 7, about 2 to about 7, about 3 to about 7, about 4 to about 7, about 5 to about 7, about 1 to about 6, about 2 to about 6, about 3 to about 6, about 4 to about 6, about 5 to about 6, about 1 to about 5, about 2 to about 5, about 3 to about 5 or about 4 to about 5 bar).

In various embodiments nanofiltration is conducted using a membrane having a molecular weight cutoff of at least about 0.1, 0.2, 0.25, 0.3, 0.4, 0.5, 0.6, 0.7, 0.8, 0.9 or 1 kDa, and useful ranges may be selected from between any of these values, (for example, about 0.1 to about 1, about 0.1 to about 0.8, about 0.1 to about 0.5, about 0.1 to about 0.4, about 0.1 to about 0.3, about 0.1 to about 0.25, about 0.1 to about 0.2, about 0.2 to about 1, about 0.2 to about 0.6, about 0.2 to about 0.5, about 0.2 to about 0.3, about 0.2 to about 0.25, about 0.3 to about 1, about 0.3 to about 0.8, about 0.3 to about 0.6, about 0.3 to about 0.5, about 0.4 to about 1, about 0.4 to about 0.6, about 0.5 to about 1, about 0.5 to about 0.8, about 0.6 to about 1, about 0.6 to about 0.7, about 0.7 to about 1 kDa).

In various embodiments nanofiltration is conducted at a temperature of at least about 15, 20, 25, 30, 35, 40, 45, 50, 55, 60, 65, 70 or 75° C., and useful ranges may be selected from between any of these values, (for example, from about 15 to about 75, about 20 to about 75, about 25 to about 75, about 15 to about 70, about 20 to about 70, about 25 to about 70, about 15 to about 65, about 20 to about 65, about 25 to about 65, about 15 to about 60, about 20 to about 60, about 25 to about 60, about 15 to about 55, about 20 to about 55, or about 25 to about 55° C.).

Suitable membranes for nanofiltration include polyamide-imide membranes or polyamide thin film composite membranes. Suitable polyamide-imide membranes include the Synder® NF membranes, including the Synder® NFS, NFX and NFW membranes. Other nanofiltration membranes known in the art may also be suitable as will be apparent to those skilled in the art.

In various embodiments nanofiltration is conducted using a membrane having a molecular weight cutoff of at least about 10, 25, 50, 100, 150, 200, 250, 300, 350, 400 or at least about 500 Da, and useful ranges may be selected from between any of these values, (for example, from about 10 to about 500, about 50 to about 500, about 100 to about 500, about 10 to about 400, about 50 to about 400, about 100 to about 400, about 10 to about 300, about 50 to about 300, about 100 to about 300, about 10 to about 250, about 50 to about 250, or about 100 to about 250 Da).

In various embodiments nanofiltration is conducted at a pressure of at least about 5, 10, 15, 20, 25, 30, 35, 40, 45, 50, 55, 60, 65, 70 or at least about 75 bar, and useful ranges may be selected from between any of these values, (for example, from about 5 to about 75, about 30 to about 75, about 35 to about 75, about 5 to about 70, about 30 to about 70, about 35 to about 70, about 5 to about 65, about 30 to about 65, about 35 to about 65, about 5 to about 60, about 25 to about 60, about 30 to about 60, about 35 to about 60, about 40 to about 60, about 5 to about 55, about 25 to about 55, about 30 to about 55, about 35 to about 55, about 40 to about 55, about 5 to about 50, about 25 to about 50, about 30 to about 50, about 35 to about 50, about 40 to about 50, about 5 to about 45, about 25 to about 45, about 30 to about 45, about 35 to about 45, or about 40 to about 45 bar).

3. Disaccharide Removal

Various methods may be used to separate disaccharides, particularly lactose, from sialyloligosaccharides in the sialyloligosaccharide-containing source material.

3.1 Enzyme Reaction

In some embodiments the method comprises an enzyme reaction to increase or decrease the molecular size of one or more disaccharides to produce one or more monosaccharides or oligosaccharides.

The reaction product may be subjected to filtration to remove the monosaccharides or oligosaccharides produced by the enzyme reaction. Methods to measure oligosaccharides such as galactooligosaccharides are given by "AOAC official method of 2001. 02 trans-Galactooligosaccharides (TGOS)," in Selected Food Products, AOAC International, Gaithersburg, Md., USA, 2005." Any suitable method designed for this purpose could also be used. Suitable filtration conditions are discussed above. Filtration conditions, for example, membrane pore size or molecular weight cutoff, temperature and pressure, are selected such that the monosaccharides or polysaccharides to be removed are retained in the retentate and the sialyloligosaccharides are contained in the permeate, or vice versa. Methods to measure sialyloligosaccharides' are given by Fong, B. et al., 2011. Quantification of bovine milk oligosaccharides using liquid chromatography-selected reaction monitoring-mass spectrometry. Journal of agricultural and food chemistry, 59(18), pp. 9788-9795.

In one embodiment the enzyme reaction increases the molecular size of the disaccharide to produce one or more polysaccharides. In another embodiment the enzyme reaction decreases the molecular size of the disaccharide to produce one or more monosaccharides.

In one embodiment the enzyme is a β-galactosidase. β-galactosidase catalyses the hydrolysis of the β-glycosidic bond between galactose and other sugars. The conditions of the enzyme reaction may be manipulated to produce monosaccharides and/or oligosaccharides.

The β-galactosidase can be sourced from *Kluyveromyces fragilis, Aspergillus niger, Aspergillus oryzae, Kluyveromyces lactis, Kluyveromyces* spp., *Penicillium* spp., *Rhodotorula* spp., *Sporobolomyces singularis, Bifidobacterium* spp., *Bacillus* spp., *Bacillus circulans, Escherichia coli, Lactobacillus thermophiles, Lactobacillus* spp., *Leuconostoc*, citrovorum or *Enterobacter* spp.

For example, when there is an excess of disaccharide available, transglycosylation to produce oligosaccharides may be favoured. It may be necessary to perform a concentration step before an enzyme reaction to promote transglycosylation.

In various embodiments the input material (first permeate or deminerliased liquid source) to increase the molecular size of at least one disaccharide comprises at least about 30%, 35%, 40%, 45%, 50%, 55%, 60%, 65% or at least about 70% disaccharides, particularly lactose. Suitable ranges may be selected from between any of these values, for example, from about 30% to about 70% or from about 40% to about 60%.

When there is limited disaccharide available, hydrolysis to produce monosaccharides may be favoured. In various embodiments the input material (first permeate or demineralised liquid source) to an enzyme reaction to decrease the molecular size of at least one disaccharide comprises at least about 5, 10, 15, 20, 25, 30, 35, or 40% by weight disaccharides, particularly lactose. Suitable ranges may be selected from between any of these values, for example, from about 5 to about 40 or from about 20 to about 30% by weight.

For the hydrolysis reaction, we conducted this reaction on milk permeate at 3 pH values: 6.1, 6.3, and 6.5 and at 40° C. A single enzyme addition rate was used (36735 NLU/kg of lactose). The enzyme was GODO-YLN2 from Danisco. The reaction was also undertaken on lactose mother liquor (lactose concentration of 42% w/w) at a pH of 4.28, and at two temperatures (54 and 58.5° C.). The enzyme used was 17MDP from Biocatalysts (UK). Our selection of conditions were similar to the recommended ones, but process conditions were modified to suit the enzyme. No significant variations in results were found across the different parameters tested.

In one exemplary embodiment β-galactosidase catalyses the production of galactooligosaccharides (GOS) from lactose. The reaction product may be subjected to nanofiltration to remove the GOS. In one embodiment nanofiltration is used to remove GOS and protein.

In another exemplary embodiment β-galactosidase catalyses the production of galactose and glucose from lactose. The reaction product may be subjected to nanofiltration to remove the galactose and glucose. In one embodiment nanofiltration removes galactose, glucose and soluble minerals.

In various embodiments two or more enzyme reaction steps are conducted.

For example, in one embodiment a first enzyme reaction step is conducted to produce one or more monosaccharides. A second enzyme step is conducted to produce one or more oligosaccharides.

In one embodiment the first enzyme reaction step is conducted after ceramic filtration. In another embodiment the first enzyme reaction step is conducted after demineralisation, prior to ultrafiltration.

In one embodiment the second enzyme reaction step is conducted after nanofiltration and before concentration.

4. Concentration

In various embodiments the method comprises one or more steps to concentrate the sialyloligosaccharides.

In some embodiments concentration is by removing water. Any concentration process can be used to effect this, such as nanofiltration, reverse osmosis or evaporation. Both reverse osmosis and evaporation may be used.

Evaporation for the purpose of concentration may be carried out by any suitable evaporative process. Evaporators such as a falling film evaporator, rising film evaporator, plate evaporator, or multiple effect evaporator may be used.

In some embodiments nanofiltration is used in combination with reverse osmosis.

In some embodiments, for example prior to an enzyme reaction to produce oligosaccharides, nanofiltration, reverse osmosis and evaporation are used

5. Decolourisation

In one embodiment the reaction product is subjected to decolourisation to remove impurities that cause discolouration and/or undesirable odours. Decolourisation can be determined by measuring the change in absorbance with a spectrophotometer over the visible range of wavelengths.

In one embodiment decolourisation is performed by exposing the liquid stream to activated carbon. A subsequent filtration step is conducted to remove the activated carbon from the stream. Decolourisation may be conducted as a batch or continuous process.

In various embodiments decolourisation is conducted at a temperature of at least about 25, 30, 35, 40, 45, 50, 55, 60, 65, 70, 75, 80, 85, 90 or at least about 95° C., and useful ranges may be selected from between any of these values, (for example, from about 25 to about 95, about 40 to about 95, about 50 to about 95, or about 55 to about 95° C.).

6. Crystallisation and Drying

In various embodiments at least one concentration step is performed to produce the sialyloligosaccharide-containing extract.

The sialyloligosaccharide-containing extract may be dried using suitable methods known in the art. In one embodiment the extract is subjected to crystallisation before drying.

7. Sialyloligosaccharide-Containing Compositions and Extracts

The extracts and compositions of the invention are enriched in sialyloligosaccharides and neutral oligosaccharides and are low in impurities such as lactose, protein and minerals.

Sialyloligosaccharides are oligosaccharides comprising at least one sialic acid moiety. Sialic acids are N- or O-substituted derivatives of neuraminic acid. Mammalian milk comprises both free sialyloligosaccharides and sialyloligosaccharides bound to glycoproteins and/or glycolipids.

In various embodiments the composition contains free sialic acid.

In various embodiments the composition or extract comprises 3'-sialyllactose, 6'-sialyllactose, disialyllactose, sialyllactosamine or a combination of any two or more thereof. In an exemplary embodiment the composition or extract comprises 3'-sialyllactose, 6'-sialyllactose, disialyllactose and sialyllactosamine.

In various embodiments the extract or composition comprises at least about 1, 2, 3, 4, 5, 6, 7, 8, 9, 10, 12, 15, 17, 20, 25, 30, 35 or 40% by weight sialyloligosaccharides as a percentage of the total solids, and suitable ranges may be selected from between any of these values, (for example, from about 1 to about 40, about 5 to about 40, about 7 to about 40, about 10 to about 40, about 1 to about 35, about 5 to about 35, about 7 to about 35, about 10 to about 35, about 1 to about 30, about 5 to about 30, about 7 to about 30, about 10 to about 30, about 1 to about 25, about 5 to about 25, about 7 to about 25, about 10 to about 25, about 1 to about 20, 5 to about 20, about 7 to about 20, about 10 to about 20, about 1 to about 15, about 5 to about 15, about 7 to about 15 or from about 10 to about 15% by weight sialyloligosaccharides).

In various embodiments the composition or extract comprises at least about 0.5, 1, 2, 3, 4, 5, 6, 7, 8, 9, 10, 12, 15, 17, 20, 25, 30, 35 or 40% by weight 3'-sialyllactose as a percentage of the total solids, and suitable ranges may be selected from between any of these values, (for example, from about 1 to about 40, about 5 to about 40, about 7 to about 40, about 10 to about 40, about 1 to about 35, about 5 to about 35, about 7 to about 35, about 10 to about 35, about 1 to about 30, about 5 to about 30, about 7 to about 30, about 10 to about 30, about 1 to about 25, about 5 to about 25, about 7 to about 25, about 10 to about 25, about 1 to about 20, 5 to about 20, about 7 to about 20, about 10 to about 20, about 1 to about 15, about 5 to about 15, about 7 to about 15 or from about 10 to about 15% by weight 3'-sialyllactose).

In various embodiments the composition or extract comprises at least about 0.1, 0.5, 0.75, 1, 1.25, 1.5, 1.75, 2, 2.25, 2.5, 2.75, 3, 3.5, 4, 4.5, 5, 6, 7, 8, 9, 10, 12, 15, 17 or 20% by weight 6'-sialyllactose as a percentage of the total solids, and suitable ranges may be selected from between any of these values, (for example, from about 0.1 to about 20, about 0.1 to about 15, about 0.1 to about 12, about 0.1 to about 10, about 0.1 to about 8, about 0.5 to about 20, about 0.5 to about 15, about 0.5 to about 12, about 0.5 to about 10, about 0.5 to about 8, about 1 to about 20, about 1 to about 15, about 1 to about 12, about 1 to about 10, about 1 to about 8, about 1.5 to about 20, about 1.5 to about 15, about 1.5 to about 12, about 1.5 to about 10, about 1.5 to about 8, about 2 to about 20, about 2 to about 15, about 2 to about 12, about 2 to about 10, about 2 to about 8, about 2.5 to about 20, about 2.5 to about 15, about 2.5 to about 12, about 2.5 to about 10, about 2.5 to about 8, about 3 to about 20, about 3 to about 15, about 3 to about 12, about 3 to about 10, or from about 3 to about 8% by weight 6'-sialyllactose).

In various embodiments the extract or composition comprises at least about 0.001, 0.005, 0.01, 0.02, 0.025, 0.03, 0.04, 0.05, 0.075, 0.1, 0.2, 0.25, 0.5, 0.75, 1, 1.25, 1.5, 1.75, 2% by weight disialyllactose as a percentage of the total solids, and suitable ranges may be selected from between any of these values, (for example, from about 0.001 to about 2, about 0.001 to about 1, about 0.005 to about 1.5, about 0.005 to about 1, about 0.01 to about 2, about 0.01 to about 1.5, about 0.01 to about 1.25, about 0.01 to about 1, about 0.01 to about 0.75, about 0.02 to about 2, about 0.02 to about 1.5, about 0.02 to about 1.25, about 0.02 to about 1, about 0.02 to about 0.75, about 0.03 to about 2, about 0.03 to about 1.5, about 0.03 to about 1.25, about 0.03 to about 1, about 0.03 to about 0.75, about 0.05 to about 2, about 0.05 to about 1.5, about 0.05 to about 1.25, about 0.05 to about 1, or at least about 0.05 to about 0.75% by weight disialyllactose).

In various embodiments the extract or composition comprises at least about 0.001, 0.005, 0.01, 0.02, 0.025, 0.03, 0.04, 0.05, 0.075, 0.1, 0.2, 0.25, 0.5, 0.75, 1, 1.25, 1.5, 1.75, or at least about 2% by weight sialyllactosamine as a percentage of the total solids, and suitable ranges may be selected from between any of these values, (for example, from about 0.001 to about 2, about 0.001 to about 1, about 0.005 to about 1.5, about 0.005 to about 1, about 0.01 to about 2, about 0.01 to about 1.5, about 0.01 to about 1.25, about 0.01 to about 1, about 0.01 to about 0.75, about 0.02 to about 2, about 0.02 to about 1.5, about 0.02 to about 1.25, about 0.02 to about 1, about 0.02 to about 0.75, about 0.03 to about 2, about 0.03 to about 1.5, about 0.03 to about 1.25, about 0.03 to about 1, about 0.03 to about 0.75, about 0.05 to about 2, about 0.05 to about 1.5, about 0.05 to about 1.25, about 0.05 to about 1, or at least about 0.05 to about 0.75% by weight sialyllactosamine).

In various embodiments the extract or composition comprises, on a dry solids basis, a greater amount of 3'-sialyllactose relative to the amount of 6'-sialyllactose.

In various embodiments the extract or composition comprises 3'-sialyllactose and 6'-sialyllactose in a ratio of about 10:1, 9:1, 8:1, 7:1, 6:1, 5:1, 4:1, 3:1, 2:1, 1:1 or 1:2 and suitable ranges may be selected from between any of these values, (for example, from about 10:1 to about 1:1, about 8:1 to about 1:1, about 7:1 to about 1:1, about 6:1 to about 1:1, about 5:1 to about 1:1, about 15:1 to about 2:1, about 12:1 to about 2:1, about 10:1 to about 2:1, about 8:1 to about 2:1, about 7:1 to about 2:1, about 6:1 to about 2:1, about 5:1 to about 2:1, about 15:1 to about 3:1, about 12:1 to about 3:1, about 10:1 to about 3:1, about 8:1 to about 3:1, about 7:1 to about 3:1, about 6:1 to about 3:1, or about 5:1 to about 3:1.

In various embodiments the composition or extract further comprises other sialic acid-containing compounds including milk fat globular membrane (MFGM), sialic acid-containing protein and gangliosides.

The term "sialic acid containing compounds" as used herein includes compounds such as lipids, and protein that contain bound sialic acid. Examples of sialic acid containing compounds present in the compositions or extracts described herein include proteins and gangliosides. Milk fat globular membrane is an example of a source of sialic acid containing compounds present in the compositions and extracts described herein.

In various embodiments the composition or extract comprises at least about 0.5% of other sialic acid containing compounds as a percentage of the total solids.

The compositions and extracts further comprise neutral oligosaccharides. In some embodiments the composition or extract comprises added neutral oligosaccharides.

Neutral oligosaccharides are oligosaccharides that have no charge. Neutral oligosaccharides present in the compositions of the invention include galactooligosaccharides, fructooligosaccharides, N-acetyllactosamine, N-acetylgalactosaminylglucose, N-acetylgalactosaminyllactose, isoglobotriose, 3'-galactosyllactose, 4'-galactosyllactose, 6'-galactosyllactose, novo-lacto-N-pentaose-I, Lacto-N-neotetraose, and Lacto-N-neohexaose. Fructooligosaccharides can be detected by methods such as described in Cuany, Denis, Thierry Benet, and Sean Austin. 2010 *Journal of AOAC International* 93 (10) p 202-212.

In some embodiments the composition contains added neutral oligosaccharides.

In various embodiments the extract or composition comprises at least about 0.01, 0.05, 0.1, 0.2, 0.25, 0.5, 0.75, 1, 2, 3, 4, 5, 6, 7, 8, 9, 10, 12, 15, 17, 20, 25 or 30% by weight neutral oligosaccharides, and suitable ranges may be selected from between any of these values, (for example, from about 0.01 to about 30, about 0.01 to about 20, about 0.01 to about 15, about 0.01 to about 10, about 0.01 to about 6, 0.01 to about 2, about 0.01 to about 0.5, about 0.05 to about 30, about 0.05 to about 25, about 0.05 to about 20, about 0.05 to about 15, about 0.05 to about 10, about 0.1 to about 30, about 0.1 to about 25, about 0.1 to about 20, about 0.1 to about 15, about 0.1 to about 10, about 0.2 to about 30, about 0.2 to about 25, about 0.2 to about 20, about 0.2 to about 15, about 0.2 to about 10, about 0.25 to about 30, about 0.25 to about 25, about 0.25 to about 20, about 0.25 to about 15, about 0.25 to about 10, about 0.5 to about 30, about 0.5 to about 25, about 0.5 to about 20, about 0.5 to about 15, about 0.5 to about 10, about 1 to about 30, about 1 to about 25, about 1 to about 20, about 1 to about 15, about 1 to about 10, about 2 to about 30, about 2 to about 25, about 2 to about 20, about 2 to about 15, about 2 to about 10, about 5 to about 30, about 5 to about 25, about 5 to about 20, about 5 to about 15, about 10 to about 30, about 10 to about 25, or about 10 to about 20% by weight neutral oligosaccharides).

In various embodiments the extract or composition comprises less than about 20, 19, 18, 17, 16, 15, 14, 13, 12, 11, 10, 9, 8, 7, 6, 5, 4, 3, 2 or 1% by weight protein and non-protein nitrogen, and suitable ranges may be selected from between any of these values, (for example, from about 1 to about 20, about 1 to about 15, about 1 to about 10, about 1 to about 8, about 1 to about 6, about 1 to about 5, about 2 to about 20, about 2 to about 16, about 2 to about 11, about 2 to about 9, about 2 to about 8, about 2 to about 7, about 3 to about 20, about 3 to about 15, about 3 to about 13, about 3 to about 9, about 3 to about 8, about 3 to about 6, about 4 to about 20, about 4 to about 15, about 4 to about 10, about 4 to about 9, about 4 to about 8, about 4 to about 7, about 5 to about 2,0 5 to about 16, about 5 to about 10, about 5 to about 8, about 5 to about 7, about 6 to about 20, about 6 to about 17, about 6 to about 11, about 6 to about 10, about 6 to about 9, about 7 to about 20, about 7 to about 15, about 7 to about 10, about 8 to about 20, about 8 to about 17, about 8 to about 12, about 9 to about 20, about 9 to about 15, about 10 to about 20, about 10 to about 16, about 11 to about 20 about 11 to about 16, about 12 to about 20, about 12 to about 17, about 13 to about 20, about 13 to about 16, about 14 to about 20, about 14 to about 18 or about 15 to about 20% by weight protein and non-protein nitrogen).

As used herein the term "non-sialyloligosaccharide sugars" refers to all sugars in the composition except for sialyloligosaccharides. Non-sialyloligosaccharide sugars include disaccharides (particularly lactose), monosaccharides (including glucose and galactose) and other oligosaccharides (including neutral oligosaccharides and acidic oligosaccharides).

In various embodiments the extract or composition comprises less than about 85, 84, 83, 82, 81, 80, 79, 78, 77, 75, 70, 65, 60, 55, 50, 45, 40, 35, or 30% by weight non-sialyloligosaccharide sugars, and suitable ranges may be selected from between any of these values, (for example, from about 30 to about 85, about 30 to about 80, about 30 to about 75, about 40 to about 85, about 40 to about 80, about 40 to about 75, about 50 to about 85, about 50 to about 80, about 50 to about 75, about 50 to about 70, about 55 to about 85, about 55 to about 80, about 55 to about 75, about 55 to about 70, about 60 to about 85, about 60 to about 80, about 60 to about 75, about 60 to about 70, about 65 to about 80, about 65 to about 80, about 65 to about 75, about 65 to about 70, about 70 to about 85, about 70 to about 80, or from about 70 to about 75% by weight non-sialyloligosaccharide sugars).

In various embodiments the extract or composition comprises less than about 15, 12, 10, 9, 8, 7, 6, 5, 4, 3, 2 or less than about 1% by weight ash, and suitable ranges may be selected from between any of these values, (for example, from about 0 to about 15, about 0 to about 12, about 0 to about 10, about 0 to about 7, about 0 to about 5, 1 to about 15, about 1 to about 12, about 1 to about 10, about 1 to about 7, about 1 to about 5, about 2 to about 15, about 2 to about 12, about 2 to about 10, about 2 to about 7, about 3 to about 15, about 3 to about 12, about 3 to about 10, about 3 to about 7, about 4 to about 15, about 4 to about 12, about 4 to about 10, about 4 to about 7, about 5 to about 15, about 5 to about 12, or about 5 to about 10% by weight ash).

8. Nutritional Formulations

The extracts and compositions of the invention are suitable for use in nutritional formulations including maternal formulas, infant formulas, follow-on formulas, growing-up formulas, paediatric formulas, human milk fortifiers, children's foods or drinks, maternal supplements, maternal nutritional formulations, fermented foods, UHT milks, UHT drinking yoghurts, acidified milk drinks, UHT powders, medical foods, sports nutritional formulations, or formulations for senior or aged populations.

The term "maternal formula" as used in this specification means a composition for pregnant woman to take during pregnancy. The term "infant formula" as used in this specification means a composition for infants aged between 0 days and 6 months old. The term "follow-on formula" as used in this specification means a composition for infants aged 6 months to 1 year. The term "growing up formula" as used in this specification means a composition for infants and children aged 1 year upwards. Growing-up formula includes growing-up milk powders or GUMPs. The term "paediatric formula" as used in this specification means a composition for children aged from birth.

It will be appreciated by those skilled in the art that the age ranges for the different compositions: "infant formula", "follow-on formula, "growing-up formula" and "paediatric formula" can vary from child to child depending on the individual's development. These products may be in liquid form as concentrates or ready-to-drink liquids or provided as powder concentrates.

In various embodiments the nutritional formulation comprises at least about 0.005, 0.01, 0.05, 0.1, 0.5, 1, 2, 3, 4 or 5% of the sialyloligosaccharide-containing extract or composition, and suitable ranges may be selected from between any of these values, (for example, from about 0005 to about 5, about 0.005 to about 3, about 0.005 to about 1, about 0.005 to about 0.5, about 0.005 to about 0.05, about 0.01 to about 5, about 0.01 to about 3, about 0.01 to about 1, about 0.01 to about 0.5, about 0.01 to about 0.1, about 0.05 to about 5, about 0.05 to about 4, about 0.05 to about 1, about 0.05 to about 0.1, about 0.1 to about 5, about 0.1 to about 4, about 0.1 to about 1, about 0.1 to about 0.5, about 0.5 to about 5, about 0.5 to about 3, about 0.5 to about 1, about 1 to about 5, about 1 to about 4, about 1 to about 3, about 2 to about 5, about 2 to about 4, about 3 to about 5% of the sialyloligosaccharide to about containing extract or composition).

In various embodiments the nutritional formulation comprises at least about 0.005% total sialyloligosaccharides on a weight/volume basis.

8.1 Formulas for Infants and Children

In various embodiments the infant formula comprises at least about 0.17% total sialyloligosaccharides on a weight/weight solids basis.

In various embodiments the follow-on formula comprises at least about 0.19% total sialyloligosaccharides on a weight/weight solids basis.

In various embodiments the growing-up formula comprises at least about 0.19% total sialyloligosaccharides on a weight/weight solids basis.

In various embodiments the maternal formula comprises at least about 0.15% total sialyloligosaccharides on a weight/weight solids basis.

As used herein, infant formulas refer to nutritional formulas for infants aged 0-6 months, follow-on formula for infants aged 6 months to 1 year, growing up formula for infants aged 12 months onwards. Maternal formulas are for woman trying to conceive, pregnant, or breastfeeding.

Nutritional formulations comprising the sialyloligosaccharide extracts and compositions described herein may be incorporated into formulations known in the art. Suitable formulations and ingredients will be apparent to those skilled in the art.

In one embodiment, the extract or composition delivers more humanised milk-based nutrition in relation to, for example, 3'-sialyllactose. "More humanised" means that the extract or composition is compositionally or functionally more similar to human breast milk than the unmodified or unprocessed form of the source material in relation to, for example, 3'-sialyllactose.

One example of the increased humanisation of the extract or composition is in relation to >3-4 months post-partum infants through the ratio of 3'-sialyllactose and 6'-sialyllactose.

The applicant has determined that the complement and concentration of sialyloligosaccharides for infants and children varies at different ages and stages of development. In particular, the ratio of 3'-sialyllactose and 6'-sialyllactose varies as the infant or child develops.

In one embodiment, the optimal ratio of 3'-sialyllactose and 6'-sialyllactose may be administered in compositions specifically tailored for infants or children in particular age groups or developmental stages.

In one embodiment the composition provides a greater amount of 3'-sialyllactose than 6'-sialyllactose infants aged 4-6 months and above.

In other embodiments the composition provides nutrition to an infant of less than 3 months of age comprising 3'-sialyllactose and 6'-sialyllactose in a ratio of from about 10:1 to about 1.5:1. In one embodiment the composition is an infant formula.

In various embodiments the composition is a composition for providing nutrition to an infant of less than 6 months of age comprising 3'-sialyllactose and 6'-sialyllactose in a ratio of from about 10:1 to about 1.5:1. In one embodiment the composition is an infant formula.

In various embodiments the composition is a composition for providing nutrition to an infant of from about 6 months to about 12 months of age comprising 3'-sialyllactose and 6'-sialyllactose in a ratio of from about 10:1 to about 1.5:1. In one embodiment the composition is an follow-on formula.

In various embodiments the composition is a composition for providing nutrition to an infant of 12 months of age or over comprising 3'-sialyllactose and 6'-sialyllactose in a ratio of from about 10:1 to about 1:2. In various embodiments the composition is a growing up formula or a paediatric formula.

A paediatric formula is given by way for example below.

| Nutrients | Average quantity per 100 mL of prepared formula |
|---|---|
| Energy | 280 kJ |
| Protein | 1.7 g |
| Fat | 3.4 g |
| Linoleic Acid | 496 mg |
| alpha Linolenic Acid | 58.6 mg |
| Docosahexaenoic Acid (DHA) | 7.2 mg |
| Arachidonic Acid (ARA) | 9.0 mg |
| Carbohydrate | |
| Lactose | 7.4 g |
| 3'-and 6'-Sialyllactose | 40.7 mg |
| Sialyllactosamine | 3.3 mg |
| Vitamins | |
| Vitamin A | 64.1 μg RE |
| Vitamin B6 | 51.5 μg |
| Vitamin B12 | 0.5 μg |
| Vitamin C | 11.7 mg |
| Vitamin D3 | 0.9 μg |
| Vitamin E | 1.5 mg TE |
| Vitamin K1 | 6.4 μg |
| Biotin | 4.3 μg |
| Niacin (B3) | 636 μg |
| Folate | 13.4 μg |
| Pantothenic Acid (B5) | 624 μg |
| Riboflavin (B2) | 155 μg |
| Thiamin (B1) | 67.4 μg |
| Minerals | |
| Calcium | 64.7 mg |
| Copper | 54.8 μg |
| Iodine | 11.9 μg |
| Iron | 0.8 mg |
| Magnesium | 8.3 mg |
| Manganese | 11.6 μg |
| Phosphorus | 43.1 mg |
| Selenium | 2.3 μg |
| Zinc | 0.6 mg |
| Chloride | 65.1 mg |

-continued

| Nutrients | Average quantity per 100 mL of prepared formula |
|---|---|
| Potassium | 77.4 mg |
| Sodium | 23.4 mg |
| Other Nutrients | |
| Choline | 12.1 mg |
| Inositol | 10.4 mg |
| Taurine | 5.9 mg |
| Prebiotics (FOS) | 73.4 mg |
| Nucleotides | |
| Adenosine 5' monophosphate | 0.9 mg |
| Cytidine 5' monophosphate | 1.4 mg |
| Inosine 5' monophosphate | 0.5 mg |
| Uridine 5' monophosphate | 0.7 mg |
| Guanosine 5' monophosphate | 0.2 mg |

9. Maintaining or Increasing Brain Function or Development

Nutritional formulations, sialyloligosaccharide-containing extracts or compositions described herein may be administered to maintain or increase brain function or development in a normal subject.

Subjects who may benefit from administration of the formulations or compositions include neonates, infants, toddlers, children, pregnant women, breastfeeding mothers, adults, athletes, other sportspersons or the elderly.

As used herein, the term "normal subject" refers to a subject who is not suffering from a disease or condition associated with impaired brain function or development.

An "effective amount" is the amount required to confer therapeutic, prophylactic effect. The interrelationship of dosages for animals and humans (based on milligrams per meter squared of body surface) is described by Freireich, et al. (1966). Body surface area can be approximately determined from height and weight of the subject. See, e.g., Scientific Tables, Geigy Pharmaceuticals, Ardley, N.Y., 1970, 537. Effective doses also vary, as recognized by those skilled in the art, dependent on route of administration, carrier usage, and the like.

As used herein, the terms "to maintain brain function or development" or "maintaining brain function or development" are used interchangeably and generally refer to preventing the decline of or maintaining brain function, maintaining normal brain development or preventing delay in brain development. These terms include preventing delayed brain development, maintaining the viability or function of neuronal cells, maintaining cognitive development, preventing delayed cognitive development, maintaining cognitive performance, preventing cognitive decline, maintaining or preventing decline of learning ability, memory or attention span, maintaining the ability of a subject to cope with stress, maintaining the level of gangliosides in the brain, maintaining the level of protein-bound sialic acid in the brain e.g. Neural Cell Adhesion Molecule (NCAM), maintaining blood, nutrient or oxygen flow to the brain, maintaining synaptogenesis, maintaining the activity of the gut/brain axis, or maintaining neurogenesis.

As used herein, the terms "to increase brain health or development" or "increasing brain health and development" are used interchangeably herein and generally refer to enhancing or improving brain function and advancing brain development. These terms include increasing cognitive development or performance, increasing learning, memory or attention span, increasing the ability of a subject to cope with stress, increasing the level of gangliosides in the brain, increasing the level of protein-bound sialic acid in the brain e.g. Neural Cell Adhesion Molecule (NCAM), increasing blood, nutrient or oxygen flow to the brain, increasing synaptogenesis, increasing the activity of the gut/brain axis or increasing neurogenesis.

Optimal cognitive development is a key part of infant and child development. Therefore any agent shown to increase cognitive development will have wide benefits for infants and children.

A wide variety of methods to assess cognitive development are well known to those skilled in the art. It will be apparent that particular methods may be preferred depending on the nature of the cognition to be assessed, the characteristics or identity (such as but not limited to the species, age, health or wellbeing) of the subject, or other factors as may be applicable. For example, methodology useful for the assessment of cognitive development in non-human subjects includes the Morris Water Maze Test and the Novel Object Recognition Task Test, as described in Example 1. Examples of methodology useful for the assessment of cognitive development in human subjects includes the tools summarised in Table 1.

TABLE 1

Examples of methods for assessment of human development

| Parameter | Tool used | Age group | Components of tool | Reference |
|---|---|---|---|---|
| Cognitive and Motor Development. | Bayley Scales of Infant Development, Version 2, | 0-3 years | Global assessments of cognitive and motor development assesses the motor (fine and gross), language (receptive and expressive), and cognitive development | The Essentials of Bayley Scales of Infant Development II Assessment, Maureen M. Black, Kathleen Matula. New York: John Wily, 1999. ISBN: 978-0-471-32651-9 |

TABLE 1-continued

Examples of methods for assessment of human development

| Parameter | Tool used | Age group | Components of tool | Reference |
|---|---|---|---|---|
| Intelligence Quotient | Weschler Preschool & primary scale | 2.6-7.3 years | Verbal comprehension | WPPSI (Wechsler Preschool and Primary Scale of Intelligence - Third Edition, 2002) published: Harcourt Assessment, David Wechsler |
| Memory | Children's Memory Scale | 5-8 years | 1. Attention and working memory 2. Verbal and Visual memory 3. Short Delay and long delay 4. Recall and recognition 5. Learning Characteristics | Children's Memory Scale (CMS) 1997, Morris Cohen |
| Development | Denver Developmental Materials | 0-6 years | General childhood development | www.denverii.com |
| Executive functioning | Wisconsin card sorting test | 5+ years | 1. Preservative thinking 2. Assess abstract reasoning | Wisconsin Card Sorting Test: Computer Version 4 (WCST: CV4), Robert K. Heaton. |
| Academic Achievement | School Report Cards | 4-7 years | School Performance | Report Cards (Academic Performance in School Setting), Young Children Achievement Test, Wayne P. Hresko |

In one embodiment the administration of the composition of the invention to an individual leads to an increase in glycerophosphorylcholine (GPC) in the brain in that individual of at least about 10, 15, 20, 25, 30, 35, 40 or 50%, and suitable ranges may be selected from between any of these values.

In one embodiment the administration of the composition of the invention to an individual leads to an increase in glutamine (Glu) in the brain in that individual of at least about 10, 15, 20, 25, 30, 35, 40 or 50%, and suitable ranges may be selected from between any of these values.

In one embodiment the administration of the composition of the invention to an individual leads to an increase in myo inositol (Ins) in the brain in that individual of at least about 10, 15, 20, 25, 30, 35, 40 or 50%, and suitable ranges may be selected from between any of these values.

In one embodiment the administration of the composition of the invention to an individual leads to a decrease in Lip09 in the brain in that individual of at least about 10, 15, 20, 25, 30, 35, 40 or 50%, and suitable ranges may be selected from between any of these values.

In one embodiment the administration of the composition of the invention to an individual leads to a decrease in macromolecules (MM) in the brain in that individual of at least about 10, 15, 20, 25, 30, 35, 40 or 50%, and suitable ranges may be selected from between any of these values.

In one embodiment the administration of the composition of the invention to an individual leads to an increase in N-Acetylaspartylglutamic acid (NAAG) in the brain in that individual of at least about 10, 15, 20, 25, 30, 35, 40 or 50%, and suitable ranges may be selected from between any of these values.

In one embodiment the administration of the composition of the invention to an individual leads to an increase in the glutamate-glutamine complex (Glx) in the brain in that individual of at least about 10, 15, 20, 25, 30, 35, 40 or 50%, and suitable ranges may be selected from between any of these values.

10. Cognitive Disease

In one embodiment the extract or composition of the present invention can be used to treat or improve diseases that include cognitive decline as a symptom. For example, the use of the extract or composition can reduce the rate of cognitive decline, maintain cognition in the patient, or improve cognitive ability in that patient. Examples of diseases that include cognitive decline as a symptom of that disease include Alzheimer's disease, Parkinson's disease, Huntington's disease or dementia.

Therefore, in one embodiment the invention relates to the use of a extract or composition as described in the treatment or prevention of cognitive decline associated with any one or more or age-related cognitive decline, dementia, Alzheimer's disease, vascular disease, frontotemporal lobar degeneration (FTLD), dementia with Lewy bodies, Parkinson's disease, amyotrophic lateral sclerosis, Huntington's disease, cognitive impairment associated with schizophrenia, chemotherapy-induced neuropathy, Down's syndrome, Korsakoff's disease, cerebral palsy, epilepsy, neuronal ischemia, neuronal reperfusion injury, neuronal trauma, neuronal haemorrhage, neuronal infection, stroke, neuronal exposure to a toxic substance, age-related mental disorders, anxiety disorders, age-related depression, dementia associated with microvascular disorders (such as diabetes, hypotension, stroke induced vascular dementia, and obesity), dementia associated with a disorder of the immune system, dementia associated with a central nervous system (CNS) disorder, dementia associated with hypotension, dementia associated with obesity or vascular dementia, infantile onset severe development delay (associated with mutations with the gene encoding for N-acetylneuraminic acid) or distal myopathy with rimmed vacuoles (DMRV) comprising administering an effective amount of a sialyloligosaccharide-containing extract produced.

Example 1

Sialyloligosaccharide-containing extracts are produced using four different methods. The sialyloligosaccharide, protein, non-protein nitrogen, lactose and ash content is determined.

1. Method A

A sialyloligosaccharide-containing material comprising the mother liquor from lactose crystallisation is provided.

The source material is heated at greater than 67° C. for at least two minutes to precipitate minerals in the mother liquor. Insoluble minerals and some protein are removed by centrifugation.

The demineralised source material is subjected to an enzyme reaction step with β-galactosidase to degrade lactose to galactose and glucose.

Ultrafiltration is performed at 50° C. to 70° C., 2-10 bar using a membrane with a pore size of 3-20 kDa to remove protein.

The ultrafiltration permeate comprising saccharides, soluble minerals and sialyloligosaccharides is subjected to nanofiltration/diafiltration performed at 25-55° C., 30-50 bar using a membrane with a pore size of 100-250 Da to remove galactose, glucose and soluble minerals.

The nanofiltration retentate enriched in sialyloligosaccharides is subjected to evaporation to produce a concentrated retentate. Optionally, reverse osmosis and/or nanofiltration are performed prior to evaporation.

Optionally, a second enzyme reaction is conducted using β-galactosidase to produce glucose and galactose or to produce GOS.

The concentrated retentate or enzyme product is subjected to decolourisation and optionally filtration to produce a sialyloligosaccharide-enriched liquid extract.

The liquid extract is optionally dried to produce a dried extract. Optionally, the liquid extract is crystallised before drying.

2. Method B

A sialyloligosaccharide-containing material comprising the mother liquor from lactose crystallisation is provided.

The source material is heated at greater than 67° C. for at least two minutes to precipitate minerals in the mother liquor. Insoluble minerals and some protein are removed by centrifugation.

The demineralised source material is subjected to ultrafiltration performed at 50-70° C., 2-10 bar using a membrane with a pore size of 3-20 kDa to remove protein.

The ultrafiltration permeate comprising sugars, soluble minerals and sialyloligosaccharides is subjected to nanofiltration/diafiltration performed at 25° C.-55° C., 30-50 bar using a membrane with a pore size of 100-250 Da to remove small sugars and soluble minerals.

The nanofiltration retentate enriched in sialyloligosaccharides is subjected to evaporation to produce a concentrated retentate. Optionally, reverse osmosis and/or nanofiltration are performed prior to evaporation.

An enzyme reaction is conducted using β-galactosidase to produce glucose and galactose or to produce GOS.

The enzyme product is subjected to decolourisation and filtration to produce a sialyloligosaccharide-enriched liquid extract.

The liquid extract is optionally dried to produce a dried extract. Optionally, the liquid extract is crystallised before drying.

3. Method C

A sialyloligosaccharide-containing material comprising the mother liquor from lactose crystallisation is provided.

The source material is heated at greater than 67° C. for at least two minutes to precipitate minerals in the mother liquor.

The source material is subjected to ceramic filtration performed at 50° C. to 90° C., 1-6 bar using a membrane with a pore size/MWCO of 300 Da to 2 μm to remove insoluble minerals and protein.

The demineralised, deproteinised material is subjected to an enzyme reaction step with β-galactosidase to degrade lactose to galactose and glucose.

The material is subjected to nanofiltration/diafiltration performed at 25-55° C., 30-50 bar using a membrane with a pore size of 100-250 Da to remove galactose, glucose and soluble minerals.

The nanofiltration retentate enriched in sialyloligosaccharides is subjected to evaporation to produce a concentrated retentate. Optionally, reverse osmosis and/or nanofiltration are performed prior to evaporation.

Optionally, a second enzyme reaction is conducted using β-galactosidase to produce glucose and galactose or to produce GOS.

The concentrated retentate or enzyme product is subjected to decolourisation and optionally filtration to produce a sialyloligosaccharide-enriched liquid extract.

The liquid extract is optionally dried to produce a dried extract. Optionally, the liquid extract is crystallised before drying.

4. Method D

A sialyloligosaccharide-containing material comprising the mother liquor from lactose crystallisation is provided.

The source material is heated at greater than 67° C. for at least two minutes to precipitate minerals in the mother liquor.

The source material is subjected to ceramic filtration performed at 50-90° C., 1-6 bar using a membrane with a pore size/MWCO of 300 Da to 2 μm to remove insoluble minerals and protein.

The demineralised, deproteinised material is subjected to nanofiltration/diafiltration performed at 25-55° C., 30-50 bar using a membrane with a pore size of 100-250 Da to remove sugars and soluble minerals.

The nanofiltration retentate enriched in sialyloligosaccharides is subjected to evaporation to produce a concentrated retentate. Optionally, reverse osmosis and/or nanofiltration are performed prior to evaporation.

A second enzyme reaction is conducted using 3-galactosidase to produce glucose and galactose or to produce GOS.

The enzyme product is subjected to decolourisation and optionally filtration to produce a sialyloligosaccharide-enriched liquid extract.

The liquid extract is optionally dried to produce a dried extract. Optionally, the liquid extract is crystallised before drying.

5. Results

The composition of the sialyloligosaccharide-enriched extracts produced by methods A-D is set out in Table 1.

TABLE 1

Composition of sialyloligosaccharide-containing extracts produced by methods A-D

| Component | % by weight on a dry solids basis |
|---|---|
| Sialyloligosaccharides | 5-30% |
| 3'-sialyllactose | 5-30% |
| 6'-sialyllactose | 2-10% |
| disialyllactose | 0.01-1% |
| sialyllactosamine | 0.01-1% |
| Protein and non-protein nitrogen | 5-25% |
| Sugars excluding sialyloligosaccharides | 20-80% |
| Ash | 0-5% |

Example 2

An animal model (piglets) was used to determine the effect of sialyloligosaccharide-enriched compositions on cognition.

1. Animal Model

The brain structure and function of piglets closely resembles that of preterm human infants (Pond, et al., *Proc. Soc. Exp. Biol. Med.*, 2000. 223(1): p. 102-8; Moughan, et al., *World Rev. Nutr. Diet*, 1992. 67: p. 40-113).

The newborn piglet, similar to humans, is less developed and its body weight is relatively small in relation to its mature weight. For this reason, both newborn piglets and low-birth-weight infants are vulnerable to developmental deficits post-partum. It has been reported that naturally farrowed piglets born small for gestational age (SGA) (0.7-1.0 kg BW) have spatial learning deficits and abnormal development of white matter (Radlowski et al., *PLoS One*, 2014. 9(3): p. e91951). The piglet is a tractable translational model that can be used to investigate SGA-associated cognitive deficits and potential interventions. Moreover, the piglet's digestive system shares similar physiology and anatomical structure with human infants, and has comparable nutrient requirements.

2. Trial Design

Three-day-old male domestic piglets (n=48) were randomised to one of three groups (n=16/group) and fed formula comprising different sialyloligosaccharides from 3 to 37 days of age. The trial groups are described in Table 2.

The piglets were housed two per pen in a temperature-conditioned room on a 12-h light (08:00-20:00) and dark (20:00-08:00) cycle.

180 g of SL enriched milk powder (or plain milk powder for control) was mixed with 850 mL of warm water to form the formulation. The piglets then received 285 mL formula/kg/day for the first two weeks and 230 mL/kg/day for the remaining weeks at 8:00 h, 13:00 h, 18:00 h and 22:30 h, with an extra 50 mL formula/kg/day supplied at the last feeding.

TABLE 2

Trial Groups

| | Composition of administered formula | | | |
|---|---|---|---|---|
| Group | Total sialyloligo-saccharides | 3'sialyllac-tose | 6'-sialyllac-tose | 6'sialyllac-tosamine |
| Group 1 | Control Group | — | — | — |
| Group 2 | 9.5 g/kg of powder | 7.6 g/kg of powder | 1.9 g/kg of powder | — |
| Group 3 | 9.5 g/kg of powder | 7.0 g/kg of powder | 1.7 g/kg of powder | 0.72 g/kg of powder |

Body weight, milk intake and health status of the piglets was assessed daily. Blood samples were collected at time of euthanasia for determination of cortisol and sialyloligosaccharide levels in red blood cell (RBC) membranes.

3. Brain Sample Collection

At day 38-39 of age, piglets were euthanased by injection with lethabarb without recovering from the anaesthesia of 2-3.5% isoflurane for MRS scan. Tissue samples from different region of the brain were collected and stored at −80° C. Analysis was conducted on these samples using methods described previously (see Chen, et al. *Molecular Neurobiology* 2015. 52(1): p. 256-269; Chen et al., *Br. J. Nutr.*, 2014. 111(2): p. 332-41; Wang et al., *Am. J. Clin. Nutr.*, 2007. 85(2): p. 561-9;

4. Discrimination Testing 4.1 Methods

Two tests were undertaken: an 'easy' task (Task 1) and a more 'difficult' task (Task 2) using an 8-arm radial maze.

For both tasks, accessible milk was provided in one arm and inaccessible milk in the remaining 7 arms so that all arms have the same smells, in order to prevent olfactory learning.

For both tasks, a visual cue consisting of three black dots placed on the door with accessible milk in the arm.

For Task 1, a single black dot visual cue was placed on the remaining seven doors with inaccessible milk. For Task 2, a visual cue with two black dots was placed on the remaining seven doors.

40 trials for each task were conducted over a 10-day period beginning on day 23. Each piglet was introduced into the 8-arm radial maze individually.

Assessment of learning capacity was determined based on the number of trials taken to successfully learn the visual cue. Learning was quantified using the number of mistakes and successes in finding the accessible milk arm during each trial. A mistake was registered each time the piglet enters or puts its whole head through the wrong door. A success was registered when the piglet enters the correct door. The criterion to learn the visual cue is a maximum of one mistake in three consecutive trials. An overhead video camera records continuously during the learning and memory test and a trained observer records the results manually. All the tests are conducted by trained staff blinded to trial group. Results were corroborated by independent analysis of the video material.

To reduce stress and familiarise the piglets with the test protocol, two piglets from the same pen were allowed to enter the maze at the start of the learning period.

4.2 Results

Figure 3:
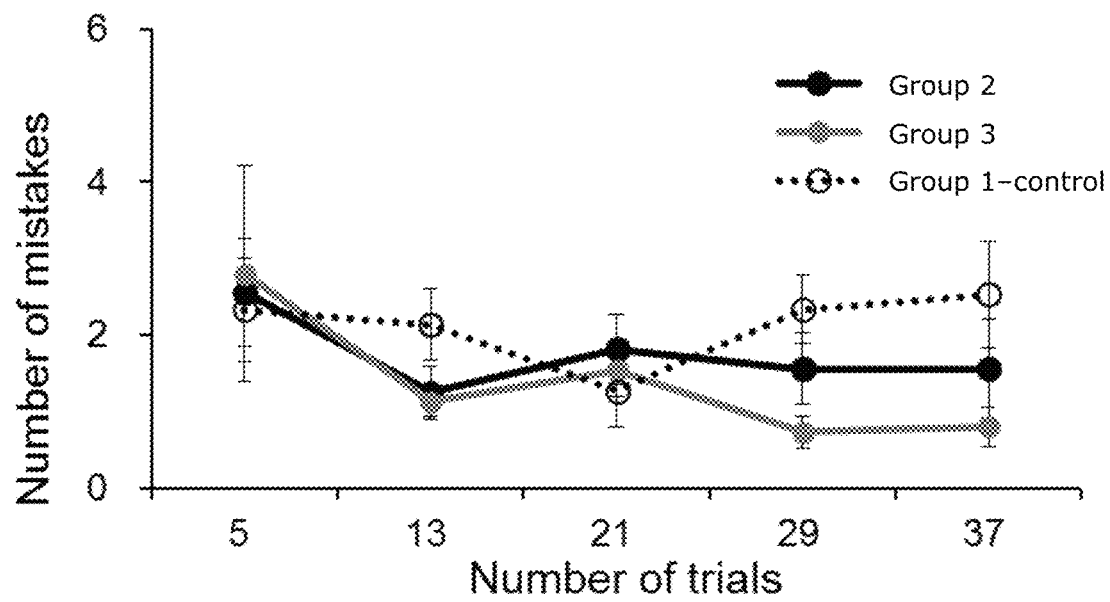
FIG. 3 shows a graph reporting the results of discrimination tests using a 3 hour "more difficult" task using an 8-arm radial maze.

There was no significant difference in the 5 min short-term memory test between the groups. The Group 3 piglets performed better in the 3 hr long-term memory trial as shown in FIG. 3.

Figure 4:
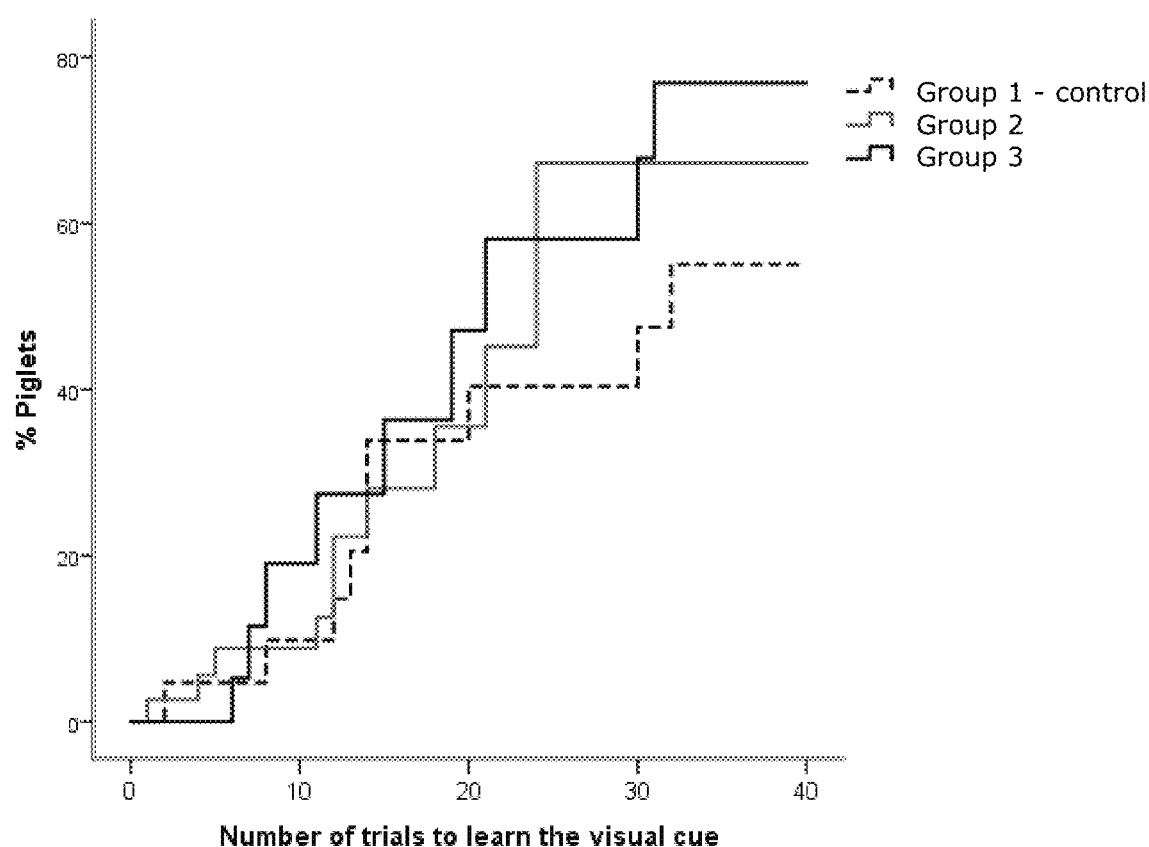
FIG. 4 shows a graph reporting the results of learning ability on a difficulty tasks using a learning criteria of a maximum of one mistake within four consecutive trials.
Figure 5:
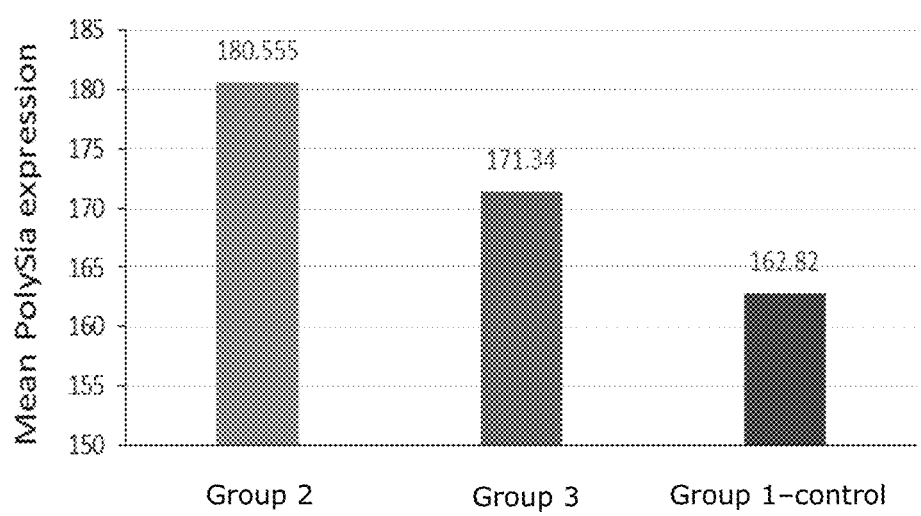
FIG. 5 shows a graph reporting PolySia expression in the frontal cortex in two treatment group compared with control.

As shown in FIG. 4, the Group 3 piglets performed better in the difficulty task based on the criteria of no more than one mistake over four consecutive trials with P<0.05 using Cox regression analysis.

5. Structural and Metabolic Assessment of the Brain Using Magnetic Resonance Spectroscopy (MRS)

5.1 Methods

Proton magnetic resonance spectroscopy ($^1$H-MRS) was performed to assess local cerebral metabolism. In vivo MRI is a powerful tool that enables morphometric imaging of the postnatal piglet brain.

Briefly, the animals were placed in right lateral position in a 3T MR scanner (Siemens Skyra, Erlangen) using a 15-channel RF coil for both RF transmission and receive. Anaesthesia was maintained with 2-3.5% isoflurane during the entire MRI scanning procedure using an Anaesthesia Machine (MPI, U.S.A.). The voxel size was 15×14×20 mm$^3$ on frontal lobe grey matter and white matter (Left to Right 15 mm, Superior to Inferior 14 mm, Anterior to Posterior 20 mm) (FIG. 1). MRS was performed using a localised single-voxel spin echo Point RESolved spectroscopy (PRESS) sequence. This PRESS sequence has three slice-selective RF pulses with the form of $90°-\gamma_1-180°-(\gamma_2+\gamma_3)-180°-\gamma_4-SE$, $\gamma_1=\gamma_2$ and $\gamma_3=\gamma_4$. The TE of the SE in this PRESS sequence is equal to $\gamma_1+\gamma_2+\gamma_3+|\gamma_4$. In this study, the TR was 2000 ms, there were three TE used: 35 ms (FIG. 1B), 135 ms (FIG. 1C) and 270 ms (FIG. 1D).

Cerebral development was assessed using 3D volumetric MRI to quantify the absolute volume of cerebral white matter, cortical gray matter and basal structures such as the striatum.

Diffusion weighted-imaging (DWI) and diffusion-tensor imaging (DTI) was performed to assess the microstructural organisation and development of the brain.

Changes in cerebral development was assessed using in vivo MR techniques using a 3.0 Tesla scanner (Siemens). Analytical methods included 3D volumetric MRI (macrostructure assessment), diffusion weighted-imaging and diffusion-tensor imaging (microstructure assessment), in conjunction with H$^1$-MR Spectroscopy (local cerebral metabolism) using a whole brain template, tissue-specific probability maps and anatomical labelling maps reported in Gan, et al. *Magn Reson Imaging* 32.10 (2014): 1396-1402.

5.2 Results

Group 3 showed a significant increase in the absolute levels of glutamate (Glu), myo-inositol (Ins) and glutamate+ glutamine (Glx). In addition, there was a significant positive correlation between frontal lobe Ins, N-acetylaspartate (NAA), total NAA, total choline (TCho), total glutathione (Glth), phosphorylcholine (PCh) and total white matter volume or whole brain volume (P<0.01).

Glutamate is the brain's major excitatory neurotransmitter, and plays an important role in frontal-hippocampal mechanism of learning and memory. Studies suggest that fast learners are characterised by an early peak in modulated glutamate compared to slow learners (Stanlet J et al., Functional dynamics of hippocampal glutamate during associative learning assessed with in vivo 1H functional magnetic resonance spectroscopy. 2017 *Neuroimage* 153: 1: 189-197).

Myo-inositol has been implicated in a role in brain development including learning and memory. Abnormally low myo-inositol and glutamate levels in the hippocampus and amygdala have been detected in patients with depression. Glutamate levels in the medial prefrontal cortex and amygdala have significant correlations with executive function and those in the hippocampus with memory function (Shirayama Y et al., Myo-inositol, Glutamate, and Glutamine in the Prefrontal cortex, Hippocampus and amygdala in major depression 2017 *Biological Psychiatry: Cognitive Neuroscience and Neuroimaging* 2; 2: 196-204). Significantly reduced concentrations of hippocampal absolute myo-inositol have been detected in patients at high risk for psychosis (Bakker et al., Hippocampal myo-inositol and glutamate concentrations are predictive of positive symptom severity in ultra-high risk for psychosis. 2013 *European Neuropschoparmacology* 23; 2: page S448).

Also demonstrated were trends for increased GPC (alpha glycerylphosphorylcholine). GPC has been implicated in neuroprotection (Plangar et al, Journal of Neuro-Oncology (2014) 119:2: 253-261), and has provided benefits in patients with cognitive dysfunction (Scapicchio P. (2013) International Journal of Neuroscience 123; 7) and has shown promise as a nutraceutical agent for enhancing cognitive performance and slowing cognitive decline (DeFina P et al., (2013) *Journal of Aging Research*).

TABLE 2

Mean (SE) absolute concentrations of metabolites in the different groups. A. TE 35, B. TE 135 and TE 270.

| Metabolites | Control | Group 2 | Group 3 | P-Value |
|---|---|---|---|---|
| TE35 | | | | |
| GABA | 1.455 ± 0.322 | 1.366 ± 0.272 | 1.11 ± 0.282 | |
| GPC | 0.627 ± 0.151 | 0.847 ± 0.185 | 0.921 ± 0.2 | |
| Glth | 1.011 ± 0.189 | 0.797 ± 0.175 | 0.8 ± 0.174 | |
| Glu | 3.004 ± 0.499 | 3.129 ± 0.417 | 2.249 ± 0.431 | |
| Ins | 4.508 ± 0.522 | 6.118 ± 0.352 | 5.344 ± 0.234 | 0.017 |
| Lip09 | 2.088 ± 0.355 | 1.931 ± 0.257 | 1.49 ± 0.257 | |
| Lip13a | 4.512 ± 1.087 | 3.682 ± 0.575 | 2.97 ± 0.463 | |
| Lip13b | 0.648 ± 0.445 | 0.095 ± 0.065 | 0.279 ± 0.151 | |
| Lip20 | 1.787 ± 0.437 | 1.236 ± 0.407 | 0.61 ± 0.307 | 0.112 |
| MM09 | 3.423 ± 0.593 | 2.673 ± 0.273 | 2.59 ± 0.313 | |
| MM12 | 1.669 ± 0.264 | 1.366 ± 0.298 | 1.444 ± 0.156 | |
| MM14 | 3.972 ± 1.341 | 3.433 ± 0.818 | 3.415 ± 0.673 | |
| MM17 | 0.567 ± 0.203 | 0.626 ± 0.171 | 0.445 ± 0.164 | |
| MM20 | 6.106 ± 0.859 | 7.827 ± 1.053 | 6.045 ± 0.856 | |
| NAA | 4.447 ± 0.539 | 4.513 ± 0.512 | 4.226 ± 0.519 | |
| NAAG | 2.014 ± 0.783 | 1.581 ± 0.481 | 2.188 ± 0.616 | |
| PCh | 1.169 ± 0.244 | 1.026 ± 0.228 | 0.973 ± 0.26 | |
| Scyllo | 0.706 ± 0.289 | 0.35 ± 0.058 | 0.304 ± 0.057 | |

TABLE 2-continued

Mean (SE) absolute concentrations of metabolites in the different groups. A. TE 35, B. TE 135 and TE 270.

| Metabolites | Control | Group 2 | Group 3 | P-Value |
|---|---|---|---|---|
| TNAA | 6.461 ± 0.328 | 6.095 ± 0.24 | 6.414 ± 0.249 | |
| TCho | 1.796 ± 0.129 | 1.873 ± 0.097 | 1.894 ± 0.103 | |
| Glx | 3.385 ± 0.562 | 3.656 ± 0.427 | 2.318 ± 0.453 | 0.116 |
| TLM09 | 5.511 ± 0.67 | 4.605 ± 0.393 | 4.08 ± 0.407 | |
| TLM13 | 10.801 ± 2.589 | 8.576 ± 0.908 | 8.109 ± 0.971 | |
| TLM20 | 7.893 ± 1.16 | 9.063 ± 1.133 | 6.655 ± 1.073 | |
| | | TE135ms | | |
| GABA | 1.071 ± 0.217 | 1.152 ± 0.362 | 1.131 ± 0.205 | |
| GPC | 2.28 ± 0.37 | 1.999 ± 0.411 | 1.855 ± 0.355 | |
| Glth | 1.418 ± 0.209 | 1.183 ± 0.118 | 1.111 ± 0.117 | |
| Glu | 7.081 ± 0.519 | 7.703 ± 0.359 | 7.462 ± 0.486 | |
| Ins | 13.705 ± 1.024 | 13.432 ± 0.738 | 12.466 ± 0.606 | |
| Lip09 | 0.514 ± 0.13 | 0.221 ± 0.087 | 0.054 ± 0.036 | 0.004 |
| Lip13a | 2.288 ± 0.883 | 0.552 ± 0.236 | 0.51 ± 0.357 | 0.05 |
| Lip13b | 0.367 ± 0.144 | 0.187 ± 0.099 | 0.492 ± 0.147 | |
| Lip20 | 0.005 ± 0.005 | 0 ± 0 | 0.01 ± 0.01 | |
| MM09 | 0.125 ± 0.093 | 0.276 ± 0.176 | 0.015 ± 0.015 | |
| MM12 | 0.013 ± 0.012 | 0.116 ± 0.078 | 0.126 ± 0.057 | |
| MM14 | 2.755 ± 1.856 | 1.476 ± 0.559 | 0.473 ± 0.218 | |
| MM17 | 0.299 ± 0.12 | 0.215 ± 0.106 | 0.211 ± 0.075 | |
| MM20 | 3.997 ± 0.888 | 6.136 ± 0.861 | 3.491 ± 0.809 | 0.521 |
| NAA | 9.89 ± 0.619 | 10.914 ± 0.702 | 10.015 ± 0.735 | |
| NAAG | 4.852 ± 0.634 | 4.129 ± 0.558 | 4.996 ± 0.719 | |
| PCh | 2.296 ± 0.394 | 2.754 ± 0.419 | 2.926 ± 0.413 | |
| PCr | 4.278 ± 0.402 | 3.976 ± 0.464 | 4.136 ± 0.388 | |
| Scyllo | 1.277 ± 0.116 | 1.414 ± 0.111 | 1.265 ± 0.123 | |
| Tau | 2.056 ± 0.378 | 2.071 ± 0.403 | 1.515 ± 0.363 | |
| TNAA | 14.742 ± 0.62 | 15.043 ± 0.492 | 15.011 ± 0.582 | |
| TCho | 4.576 ± 0.222 | 4.752 ± 0.174 | 4.781 ± 0.14 | |
| TCr | 10.228 ± 0.45 | 10.497 ± 0.335 | 10.338 ± 0.241 | |
| Glx | 8.783 ± 0.278 | 9.072 ± 0.334 | 8.968 ± 0.523 | |
| TLM09 | 0.639 ± 0.188 | 0.496 ± 0.241 | 0.069 ± 0.041 | 0.074 |
| TLM13 | 5.424 ± 2.583 | 2.332 ± 0.655 | 1.601 ± 0.468 | |
| TLM20 | 4.002 ± 0.889 | 6.136 ± 0.861 | 3.501 ± 0.806 | 0.079 |
| | | TE270ms | | |
| GABA | 1.009 ± 0.371 | 0.787 ± 0.382 | 0.981 ± 0.369 | |
| GPC | 2.345 ± 0.701 | 2.108 ± 0.71 | 3.902 ± 1.223 | |
| Glth | 5.664 ± 0.4 | 5.938 ± 0.406 | 5.557 ± 0.589 | |
| Glu | 11.896 ± 0.82 | 12.201 ± 0.63 | 15.245 ± 0.909 | 0.009 |
| Ins | 17.745 ± 0.961 | 19.017 ± 1.151 | 22.113 ± 1.303 | 0.031 |
| Lip09 | 0.443 ± 0.153 | 0.346 ± 0.147 | 0.241 ± 0.114 | |
| Lip13a | 0.213 ± 0.118 | 0.366 ± 0.366 | 0.456 ± 0.317 | |
| Lip13b | 0.033 ± 0.033 | 0.298 ± 0.159 | 0.44 ± 0.264 | |
| MM09 | 2.036 ± 0.256 | 2.05 ± 0.265 | 1.832 ± 0.317 | |
| MM12 | 0.044 ± 0.044 | 0.049 ± 0.047 | 0 ± 0 | |
| MM14 | 3.148 ± 0.59 | 3.143 ± 0.797 | 2.116 ± 0.732 | |
| MM17 | 0.837 ± 0.25 | 1.058 ± 0.38 | 0.536 ± 0.225 | |
| MM20 | 0.027 ± 0.027 | 1.69 ± 1.065 | 1.823 ± 1.118 | |
| NAA | 31.653 ± 1.594 | 32.794 ± 1.996 | 31.519 ± 2.647 | |
| NAAG | 8.56 ± 0.888 | 8.592 ± 0.988 | 10.979 ± 1.86 | |
| PCh | 8.739 ± 0.875 | 9.097 ± 0.773 | 7.849 ± 1.151 | |
| Scyllo | 2.796 ± 0.157 | 2.825 ± 0.229 | 3.05 ± 0.207 | |
| TNAA | 40.212 ± 1.424 | 41.386 ± 1.493 | 42.497 ± 1.554 | |
| TCho | 11.084 ± 0.51 | 11.205 ± 0.461 | 11.751 ± 0.561 | |
| Glx | 19.934 ± 0.829 | 20.122 ± 0.566 | 23.811 ± 1.126 | 0.004 |
| TLM09 | 2.073 ± 0.258 | 2.396 ± 0.27 | 2.479 ± 0.312 | |
| TLM13 | 3.013 ± 0.685 | 3.856 ± 0.781 | 3.438 ± 0.558 | |
| TLM20 | 2.55 ± 1.16 | 1.69 ± 1.065 | 0.814 ± 0.785 | |

The significant difference (P<0.05) shown above in Table 2 is based on a general linear model (univariate ANOVA) with Bonferroni's adjustment for multiple comparisons.

Thus the sialyloligosaccharides can alter many important brain metabolites and neurotransmitters required for optimising neurodevelopment in piglets.

6. Quantitative Biochemical Analyses 6.1 Method

The level of polysialic acid (polySia) was measured. PolySia is a unique polymer of sialic acid that modifies neural cell adhesion molecule (NCAM) spatiotemporally in embryonic brains, and is involved in cell migration, neural outgrowth, axonal guidance, synaptic plasticity, and the development of normal neural circuits and neurogenesis. PolySia expression is found in the olfactory bulb, hippocampus, subventricular zone, thalamus, prefrontal cortex, and amygdala, where neural plasticity, remodeling of neural connections, or neural generation is ongoing. PolySia may regulate various neurologically active molecules, such as neurotrophic factor (BDNF), growth factor (FGF2), and neurotransmitter (dopamine), to regulate their involved signaling.

Immunofluorescence was used to carry out biochemical analysis. Consecutive coronal sections of 8 µm thickness from the piglet's hippocampus and frontal cortex were prepared using a freezing microtome. Brain sections were fixed in ice-cold 4% paraformaldehyde for 15 min, rinsed in phosphate-buffered saline (PBS), and permeabilised with 0.3% Triton X-100 for 30 min, followed by blocking with 0.3% goat serum in PBS (RT). Sections were then incubated overnight (4° C.) with a primary antibody specific for detecting the polySia moiety of polySia-NCAM (1:200; MAB5324, Millipore, USA). After washing with PBS, sections were incubated with Alexa Fluor 488-conjugated secondary antibody (1:200; 115-545-075, Jackson ImmunoResearch, USA) for 1 hr. at room temperature. All sections were counterstained with DAPI (H-1200, VECTOR laboratories, USA). Images were obtained and analysed using a confocal microscope.

Western blot was used to analyse polySia-NCAM expression levels and other problem markers according to previous methods (Chen 2014, Zhu 2015). The dilution of the primary antibody (anti-polySia-NCAM antibody, MAB5324, Millipore) was 1:1000, and GAPDH was used as a control for the amount of protein loaded on each gel and detected using an anti-GAPDH mAb (MAB5718, R&D System, USA) at 0.05 µg/mL. The secondary antibody (anti-mouse IgG, A4416, Sigma-Aldrich, USA) was used as the dilution of 1:10000. Quantification of the protein bands was carried out by scanning the films using the Image Analyses Software (Quantity One, Bio-Rad, USA). The density of bands on all films was determined under non-saturating conditions.

6.2 Results

There was no significant difference in polySia-NCAM expression in hippocampus between groups using western blot method. However there was significantly higher PolySia expression in the frontal cortex in two treatment group compared with the control ($P<0.001$, one way ANOVA, FIG. 4).

The invention claimed is:

1. A sialyloligosaccharide-enriched composition, comprising on a dry solids basis
   at least about 5% by weight total sialyloligosaccharides comprising
   i) at least about 5% 3'-sialyllactose by weight of total sialyloligosaccharides,
   ii) at least about 2% 6'-sialyllactose by weight of total sialyloligosaccharides,
   iii) at least about 0.01% disialyllactose by weight of total sialyloligosaccharides,
   iv) at least about 0.01% sialyllactosamine by weight of total sialyloligosaccharides, and
   at least about 0.5% by weight free sialic acid,
   at least about 0.2% by weight neutral oligosaccharides,
   less than about 25% by weight protein and non-protein nitrogen,
   less than about 80% by weight sugars not including sialyllactose, and
   less than about 5% by weight ash.

2. The composition of claim 1 comprising, on a dry solids basis, a greater amount of 3'-sialyllactose relative to the amount of 6'-sialyllactose.

3. The composition of claim 2 comprising 3'-sialyllactose and 6'-sialyllactose in a ratio of from about 65:1 to about 1.5:1, from about 15:1 to about 1.5:1, or from about 8:1 to about 1.5:1.

4. A nutritional formulation comprising the sialyloligosaccharide-enriched composition of claim 1.

5. The nutritional formulation of claim 4, wherein the nutritional formulation is an infant formula, a follow-on formula, a growing-up formula, a paediatric formula, a human milk fortifier, a children's food or drink, a maternal supplement, a maternal nutritional formulation, a fermented food, a UHT milk, a UHT drinking yoghurt, an acidified milk drink, a UHT powder, a medical food, a sports nutritional formulation, or a formulation for senior or aged populations.

6. The nutritional formulation of claim 4 further comprising one or more dairy lipids, one or more galactooligosaccharides, one or more probiotic strains, one or more protein hydrolysates, lactoferrin, a milk fat globular membrane (MFGM) formulation, or a combination of any two or more thereof.

7. The nutritional formulation of claim 6, wherein the one or more dairy lipids comprises buttermilk, high fat whey protein concentrate, beta-serum, butter serum, or a combination of any two or more thereof.

8. The nutritional formulation of claim 6, wherein the one or more probiotic strain comprises a *Bifidobacterium lactis* or a *Lactobacillus rhamnosus* strain, or a combination of both *Bifidobacterium lactis* and *Lactobacillus rhamnosus*.

9. The nutritional formulation of claim 8, wherein the *Bifidobacterium lactis* strain comprises *Bifidobacterium lactis* HN019.

10. The nutritional formulation of claim 8, wherein the *Lactobacillus rhamnosus* strain comprises *Lactobacillus rhamnosus* HN001.

* * * * *